(12) United States Patent
Han et al.

(10) Patent No.: US 7,087,768 B2
(45) Date of Patent: Aug. 8, 2006

(54) FUMAGILLOL DERIVATIVES AND PREPARING METHOD THEREOF

(75) Inventors: Cheol-Kyu Han, Seoul (KR);
Jeong-Hyeok Yoon, Yongin (KR);
Seung-Moak Kim, Daejeon-si (KR);
Nam-Doo Kim, Incheon-si (KR);
Byung-Ha Chang, Suwon-si (KR);
Jee-Young Lee, Ahnyang-si (KR);
Tae-Bo Sim, Seoul (KR)

(73) Assignee: Equispharm Co., Ltd. (KR)

( * ) Notice: Subject to any disclaimer, the term of this patent is extended or adjusted under 35 U.S.C. 154(b) by 0 days.

(21) Appl. No.: 10/490,588

(22) PCT Filed: Jun. 11, 2002

(86) PCT No.: PCT/KR02/01102

§ 371 (c)(1),
(2), (4) Date: Mar. 23, 2004

(87) PCT Pub. No.: WO03/027104

PCT Pub. Date: Apr. 3, 2003

(65) Prior Publication Data

US 2004/0242681 A1    Dec. 2, 2004

(30) Foreign Application Priority Data

Sep. 27, 2001  (KR)  .......................... 10-2001-60017
May 29, 2002   (KR)  .......................... 10-2002-29915

(51) Int. Cl.
*C07D 303/00* (2006.01)

(52) U.S. Cl. ...................... 549/513; 549/435; 549/551; 544/238; 544/298; 546/281.7

(58) Field of Classification Search ................ 549/435, 549/513, 551; 544/298, 238; 514/475, 269, 514/252.01, 336, 465, 466; 546/281.7
See application file for complete search history.

(56) References Cited

U.S. PATENT DOCUMENTS

| 6,114,365 | A  | 9/2000  | Moretti |
| 6,218,418 | B1 | 4/2001  | Pevarello et al. |
| 6,333,308 | B1 | 12/2001 | Holzemann et al. |
| 6,458,810 | B1 | 10/2002 | Muller et al. |
| 6,762,195 | B1 | 7/2004  | Muller et al. |
| 6,864,252 | B1 | 3/2005  | Sakya et al. |

FOREIGN PATENT DOCUMENTS

| EP | 0 357 061  | 3/1990  |
| EP | 0 387 650  | 9/1990  |
| EP | 0 461 427  | 12/1991 |
| WO | WO 98/56372 | 12/1998 |

OTHER PUBLICATIONS

Kruger, EA et al, TNP-470: an angiogenesis inhibitor in clinical development for cancer, Exp. Opin. Invest. Drugs (2000) 9(6), 1383-1396.*

* cited by examiner

*Primary Examiner*—Amelia A. Owens
(74) *Attorney, Agent, or Firm*—Bachman & LaPointe, P.C.

(57) ABSTRACT

The disclosure relates to a fumagillol compound which can be usefully used not only as an angiogenesis inhibiting agent showing a superior angeogenesis inhibitory effect with less toxicity, but also as a cancer metastasis inhibitor and a therapeutic agent against cancer and other various inflammatory diseases such as rheumatic disease, psoriasis, etc., and diabetic retinopathy related to angeogeneois, and also a method for preparing the same.

11 Claims, No Drawings

FUMAGILLOL DERIVATIVES AND PREPARING METHOD THEREOF

TECHNICAL FIELD

The present invention is directed to a fumagillol derivative or a pharmaceutically acceptable salt thereof, showing excellent angiogenesis inhibitory effect, with low toxicity; a preparation method thereof; and a pharmaceutical composition comprising the same.

PRIOR ART

Angiogenesis is a phenomenon of forming new vessels at the capillary level by a series of processes, such as proliferation, infiltration and transfer, and interactions of vein endothelial cells. This phenomenon is considered to be not only a normal physiological process but also a pathological process of various diseases. Angiogenesis, properly controlled by various physiological substances, is an important physiological process, which is seen upon healing of wounded parts or formation of uterine endothelia after birth or menstruation.

However, in the uncontrolled state, angiogenesis that excessively generates novel capillary vessels is regarded as a pathological condition. Such angiogenesis is known to be closely associated with growth and metastasis of solid cancers, diabetic retinopathy, rheumatic arthritis and psoriasis [Billington, D. C. *Drug Design and Discovery*, (1991), 8, 3.].

Much research on inhibition of such angiogenesis regarded as a pathological condition has been performed. Judah Folkman of the Medical College of Harvard University suggested a new concept of treating solid cancer by inhibiting angiogenesis in 1971 [J. Folkman, *New Engl. Med.*, 185 (1971), 1182–1185]. In other words, an angiogenesis inhibitory agent is responsible for decrease or inhibition of growth of solid cancers, resulting in blocking metastasis of solid cancer. Such an angiogenesis inhibitory agent has a useful therapeutic effect for other inflammatory diseases, such as diabetic retinopathy, rheumatoid arthritis, psoriasis, etc, in addition to solid cancers.

Compounds inhibiting angiogenesis have been developed through many efforts up to the present, and so various compounds are known as novel angiogenesis inhibitory agents.

In this regard, European Pat. Nos. 0 354 787, 0 357 061 and 0 415 294, and Japanese Pat. No. JP-A01-233275 disclose fumagillol derivatives.

Further, it has been reported that 6-amino-6-deoxyfumagillol [*Chem. Pharm. Bull.*, 40, 575–579 (1992)], 6-O-acyl, 6-O-sulfonyl, 6-O-alkyl, 6-O-(N-substituted carbamoyl) fumagillol [*Chem. Pharm. Bull.*, 40, 96–101 (1992)] have angiogenesis inhibitory functions.

However, there is required a continuous development of angiogenesis inhibitory agents exhibiting excellent angiogenesis inhibitory effect with less toxicity, and having novel chemical structure.

DISCLOSURE OF THE INVENTION

Leading to the present invention, the intensive and thorough research into novel compounds having high inhibitory effect on angiogenesis, carried out by the present inventors, resulted in the finding that an aniline derivative having various substituents can be introduced to a known fumagillol, whereby a compound of the formula I, which has angiogenesis inhibitory effect and low toxicity, can be prepared.

It is therefore an object of the present invention to provide a fumagillol derivative or a pharmaceutically acceptable salt thereof, exhibiting excellent angiogenesis inhibitory effect.

It is another object of the present invention to provide a method of preparing such a fumagillol derivative.

It is a further object of the present invention to provide a pharmaceutical composition for angiogenesis inhibition, usable as an angiogenesis inhibitor, comprising a fumagillol derivative or a pharmaceutically acceptable salt thereof as a useful ingredient.

The above objects are achieved by providing the fumagillol derivative or the pharmaceutically acceptable salt thereof of the present invention.

BEST MODES FOR CARRYING OUT THE INVENTION

The present invention provides a fumagillol derivative represented by the following general formula I, or a pharmaceutically acceptable salt thereof:

Formula I

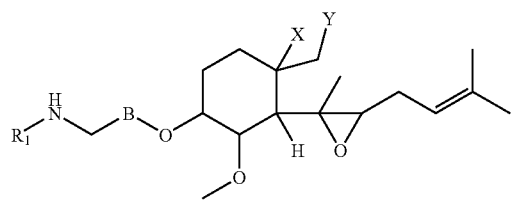

(wherein,

X is —OH and Y is halogen, or X and Y are linked together to form an oxyrane ring, B represents —(C=O)— or —CH$_2$—, R$_1$ represents hydrogen; hydroxy; —CN; —NO$_2$; —CF$_3$; formyl; C$_1$–C$_4$ thioalkyl; acetamido; acetoxy; C$_1$–C$_6$ alkyl; C$_1$–C$_4$ aminoalkyl; C$_1$–C$_4$ alkylaminoalkyl; C$_1$–C$_4$ dialkylaminoalkyl; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_6$ alkylamino; C$_1$–C$_4$ dialkylamino; C$_1$–C$_4$ hydroxyalkyl; C$_1$–C$_4$ alkyloxycarboxylic acid, or

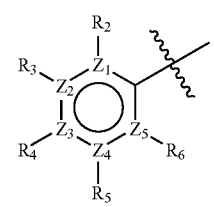

in which R$_2$, R$_3$, R$_4$, R$_5$ and R$_6$, which are the same or different, each represents hydrogen; hydroxy; —CN; —NO$_2$; —CF$_3$; formyl; C$_1$–C$_4$ thioalkyl; acetamido; acetoxy; C$_1$–C$_6$ alkyl; C$_1$–C$_4$ aminoalkyl; C$_1$–C$_4$ alkylaminoalkyl; C$_1$–C$_4$ dialkylaminoalkyl; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_6$ alkylamino; C$_1$–C$_4$ dialkylamino; C$_1$–C$_4$ hydroxyalkyl; or C$_1$–C$_4$ alkyloxycarboxylic acid; or, R$_2$ and R$_3$, R$_3$ and R$_4$, R$_4$ and R$_5$, or R$_5$ and R$_6$, are linked together to form a C$_1$–C$_3$ alkylene dioxy ring, and Z$_1$, Z$_2$, Z$_3$, Z$_4$ and Z$_5$ each represent carbon or nitrogen).

Preferably, X and Y are linked together to form the oxyran ring, and B is —(C═O)—, $R_1$ is hydrogen; hydroxy; —CN; —NO$_2$; —CF$_3$; formyl; acetamido; acetoxy; $C_1$–$C_6$ alkyl; $C_1$–$C_4$ aminoalkyl; $C_1$–$C_4$ alkylaminoalkyl; $C_1$–$C_4$ dialkylaminoalkyl; $C_1$–$C_6$ alkoxy; $C_1$–$C_6$ aminoalkoxy; $C_1$–$C_4$ alkylaminoalkoxy; $C_1$–$C_4$ dialkylaminoalkoxy; amino; $C_1$–$C_6$ alkylamino; $C_1$–$C_4$ dialkylamino; $C_1$–$C_4$ hydroxyalkyl; $C_1$–$C_4$ alkyloxycarboxylic acid, or $R_2$, $R_3$, $R_4$, $R_5$ and $R_6$, which are the same or different, each represents hydrogen; hydroxy; —CN; —NO$_2$; —CF$_3$; formyl; acetamido; acetoxy; $C_1$–$C_6$ alkyl; $C_1$–$C_4$ aminoalkyl; $C_1$–$C_4$ alkylaminoalkyl; $C_1$–$C_4$ dialkylaminoalkyl; $C_1$–$C_6$ alkoxy; $C_1$–$C_6$ aminoalkoxy; $C_1$–$C_4$ alkylaminoalkoxy; $C_1$–$C_4$ dialkylaminoalkoxy; amino; $C_1$–$C_6$ alkylamino; $C_1$–$C_4$ dialkylamino; $C_1$–$C_4$ hydroxyalkyl; or $C_1$–$C_4$ alkyloxycarboxylic acid, or $R_2$ and $R_3$, $R_3$ and $R_4$, $R_4$ and $R_5$, or $R_5$ and $R_6$ are linked together to form the $C_1$–$C_3$ alkylene dioxy ring, and $Z_1$, $Z_2$, $Z_3$, $Z_4$ and $Z_5$ each represent carbon or nitrogen.

More preferably, $R_1$ is selected from the group consisting of hydrogen; hydroxy; methyl; chlorine; methoxy; methylpropoxy; isopropoxy; allyloxy; propyloxy; acetoxy cyano; amino; dimethylaminomethyl; methylpropoxy; dimethylethoxy; 3,5-diisopropyl-4-methoxy; 3,5-dimethyl-4-methoxy; isopropyl-4-ethoxy; dimethylamino; ethylamino; methylenedioxy; nitro; acetoxy; trifluoromethyl; and hydroxyethoxy, $R_2$, $R_3$, $R_4$, $R_5$ and $R_6$ is independently selected from the group consisting of hydrogen; hydroxy; methyl; chlorine; methoxy; methylpropoxy; isopropoxy; allyloxy; propyloxy; acetoxy cyano; amino; dimethylaminomethyl; methylpropoxy; dimethylethoxy; 3,5-diisopropyl-4-methoxy; 3,5-dimethyl-4-methoxy; isopropyl-4-ethoxy; dimethylamino; ethylamino; methylenedioxy; nitro; acetoxy; trifluoromethyl; and hydroxyethoxy, and $Z_1$, $Z_2$, $Z_3$ $Z_4$ and $Z_5$ each represent carbon or nitrogen.

The fumagillol derivative of the above formula I has at least 6 chiral centers, as represented by the following formula, and in the scope of the present invention, each optical isomer or mixtures thereof is included:

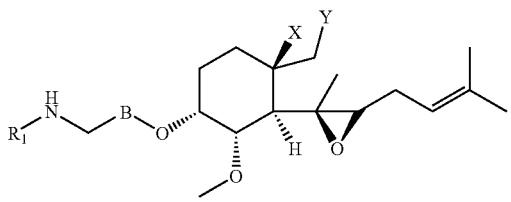

In addition, the present invention further comprises 6-O-(chloro)acetyl fumagillol as an intermediate represented by the formula II, for use in preparation of the fumagillol derivative of the formula I:

Formula II

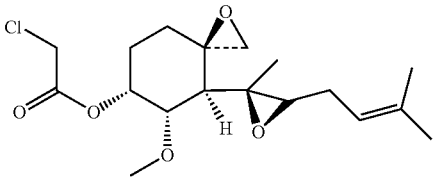

Among the compounds of the formula I, preferred are:
1) 6-O-(4-methoxyaniline)acetyl fumagillol;
2) 6-O-(3,4,5-trimethoxyaniline)acetyl fumagillol;
3) 6-O-(2,4-dimethoxyaniline)acetyl fumagillol;
4) 6-O-(3,4-dimethoxyaniline)acetyl fumagillol;
5) 6-O-(3,4-dimethoxy-6-nitroaniline)acetyl fumagillol;
6) 6-O-(3,4-dimethoxy-6-cyanoaniline)acetyl fumagillol;
7) 6-O-(4-allyloxyaniline)acetyl fumagillol;
8) 6-O-(4-(2-acetoxyethoxy)aniline)acetyl fumagillol;
9) 6-O-(3-cyano-4-methoxyaniline)acetyl fumagillol;
10) 6-O-(3-(dimethylaminomethyl)-4-methoxyaniline) acetyl fumagillol;
11) 6-O-(4-(2-methylpropoxyaniline)acetyl fumagillol;
12) 6-O-(3-isopropoxy-4-methoxyaniline)acetyl fumagillol;
13) 6-O-(4-(N,N-dimethylethoxy)aniline)acetyl fumagillol;
14) 6-O-(3,5-diisopropyl-4-methoxyaniline)acetyl fumagillol;
15) 6-O-(3,5-dimethyl-4-methoxyaniline)acetyl fumagillol;
16) 6-O-(3-isopropyl-4-ethoxy-6-methylaniline)acetyl fumagillol;
17) 6-O-(4-propyloxyaniline)acetyl fumagillol;
18) 6-O-(aniline)acetyl fumagillol;
19) 6-O-(4-chloroaniline)acetyl fumagillol;
20) 6-O-(4-dimethylaminoaniline)acetyl fumagillol;
21) 6-O-(4-hydroxyaniline)acetyl fumagillol;
22) 6-O-(4-aminoaniline)acetyl fumagillol;
23) 6-O-(3,4-methylenedioxyaniline)acetyl fumagillol;
24) 6-O-(4-nitroaniline)acetyl fumagillol;
25) 6-O-(2,3,4-trimethoxy-6-aminoaniline)acetyl fumagillol;
26) 6-O-(4-acetoxy-3,5-dimethoxyaniline)acetyl fumagillol;
27) 6-O-(3,4-dimethoxy-5-hydroxyaniline)acetyl fumagillol;
28) 6-O-(4-dimethylaminoethoxyaniline)acetyl fumagillol;
29) 6-O-(4-ethylaminoaniline)acetyl fumagillol;
30) 6-O-(4-ethylaminoethoxyaniline)acetyl fumagillol;
31) 6-O-(3-dimethylaminomethyl-4-methoxyaniline) acetyl fumagillol;
32) 6-O-(4-trifluoromethylaniline)acetyl fumagillol;
33) 6-O-(4-acetoxy aniline)acetyl fumagillol;
34) 6-O-(4-cyanoaniline)acetyl fumagillol;
35) 6-O-(4-hydroxyethoxyaniline)acetyl fumagillol;
36) 6-O-(5-amino-2-methoxypyridine)acetyl fumagillol;
37) 6-O-(5-methoxypyrimidine-2-amino)acetyl fumagillol;
38) 6-O-(3-methoxy-6-aminopyridazine)acetyl fumagillol;
39) 4-((4-methoxyaniline)acetyl)oxy-2-(1,2-epoxy-1,5-dimethyl-4-hexenyl)-3-methoxy-1-chloromethyl-1-cyclohexanol;
40) 4-((3,4,5-trimethoxyaniline)acetyl)oxy-2-(1,2-epoxy-1,5-dimethyl-4-hexenyl)-3-methoxy-1-chloromethyl-1-cyclohexanol;
41) 6-O-(ethylamino)acetyl fumagillol;
42) 6-O-(isopropyl amino)acetyl fumagillol;
43) 6-O-(1-propyl amino)acetyl fumagillol;
44) 6-O-(1-butyl amino)acetyl fumagillol;
45) 6-O-(sec-butyl amino)acetyl fumagillol;
46) 6-O-(2-methyl-butylamino)acetyl fumagillol;
47) 6-O-(t-butyl amino)acetyl fumagillol;
48) 6-O-(pentyl amino)acetyl fumagillol;
49) 6-O-(1-methyl-butyl amino)acetyl fumagillol;

50) 6-O-(1-ethyl-propyl amino)acetyl fumagillol;
51) 6-O-(1-methyl-pentylamino)acetyl fumagillol;
52) 6-O-(1,2-dimethyl-butylamino)acetyl fumagillol;
53) 6-O-(1,2,2-trimethyl-propylamino)acetyl fumagillol;
54) 6-O-(1-isopropyl-2-methylpropylamino)acetyl fumagillol;
55) 6-O-(3-methylbutylamino)acetyl fumagillol;
56) 6-O-(2-methylallylamino)acetyl fumagillol;
57) 6-O-(4-methyl-hepta-2,4-dienylamino)acetyl fumagillol;
58) 6-O-(1,5-dimethyl-4-hexenylamino)acetyl fumagillol;
59) 6-O-(1,1-dimethyl-2-propynylamino)acetyl fumagillol;
60) 6-O-(prop-2-enylamino)acetyl fumagillol;
61) 6-O-(2-bromo-ethylamino)acetyl fumagillol;
62) 6-O-(chloroethynylamino)acetyl fumagillol;
63) 6-O-(cyclopropylamino)acetyl fumagillol;
64) 6-O-(cyclobutylamino)acetyl fumagillol;
65) 6-O-(cyclopentylamino)acetyl fumagillol;
66) 6-O-(cyclohexylamino)acetyl fumagillol;
67) 6-O-(4-tert-butylcyclohexylamino)acetyl fumagillol;
68) 6-O-(2-dimethylamino-1-methylethylamino)acetyl fumagillol;
69) 6-O-(2-dimethylamino-propylamino)acetyl fumagillol;
70) 6-O-(2-methoxy-2-methyl-propylamino)acetyl fumagillol;
71) 6-O-(2-oxo-propylamine)acetyl fumagillol;
72) 6-O-(1,1-dimethyl-3-oxobutylamino)acetyl fumagillol;
73) 6-O-(ethyl-2-aminoacetate)acetyl fumagillol;
74) 6-O-(alanine-methylesteramino)acetyl fumagillol;
75) 6-O-(methyl-2-amino-3,3-dimethylbutanoate)acetyl fumagillol;
76) 6-O-(allylglycine-methylester)acetyl fumagillol;
77) 6-O-(2,2-dimethoxy-ehtylamino)acetyl fumagillol;
78) 4-((cyclopropylamino)acetyl)oxy-2-(1,2-epoxy-1,5-dimethyl-4-hexenyl)-3-methoxy-1-chloromethyl-1-cyclohexanol;
79) 4-((cyclobutylamino)acetyl)oxy-2-(1,2-epoxy-1,5-dimethyl-4-hexenyl)-3-methoxy-1-chloromethyl-1-cyclohexanol; and
80) 6-O-(chloro)acetyl fumagillol.

Among the compounds of the formula I, most preferred are:

1) 6-O-(4-methoxyaniline)acetyl fumagillol;
2) 6-O-(3,4,5-trimethoxyaniline)acetyl fumagillol;
3) 6-O-(4-(N,N-dimethylethoxy)aniline)acetyl fumagillol;
4) 6-O-(cyclopropylamino)acetyl fumagillol;
5) 6-O-(cyclobutylamino)acetyl fumagillol;
6) 4-((cyclopropylamino)acetyl)oxy-2-(1,2-epoxy-1,5-dimethyl-4-hexenyl)-3-methoxy-1-chloromethyl-1-cyclohexanol; and
7) 4-((cyclobutylamino)acetyl)oxy-2-(1,2-epoxy-1,5-dimethyl-4-hexenyl)-3-methoxy-1-chloromethyl-1-cyclohexanol.

Structural formulas of the above compounds are shown in Tables 1a to 1d, below.

TABLE 1a

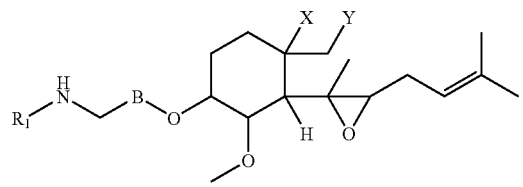

Ex. 1

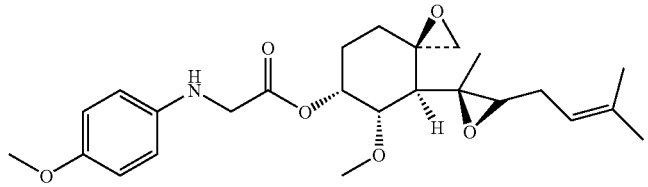

Ex. 2

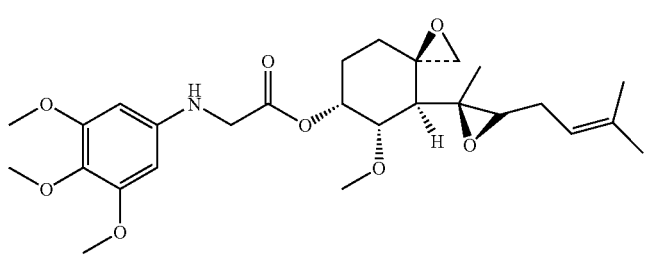

TABLE 1a-continued
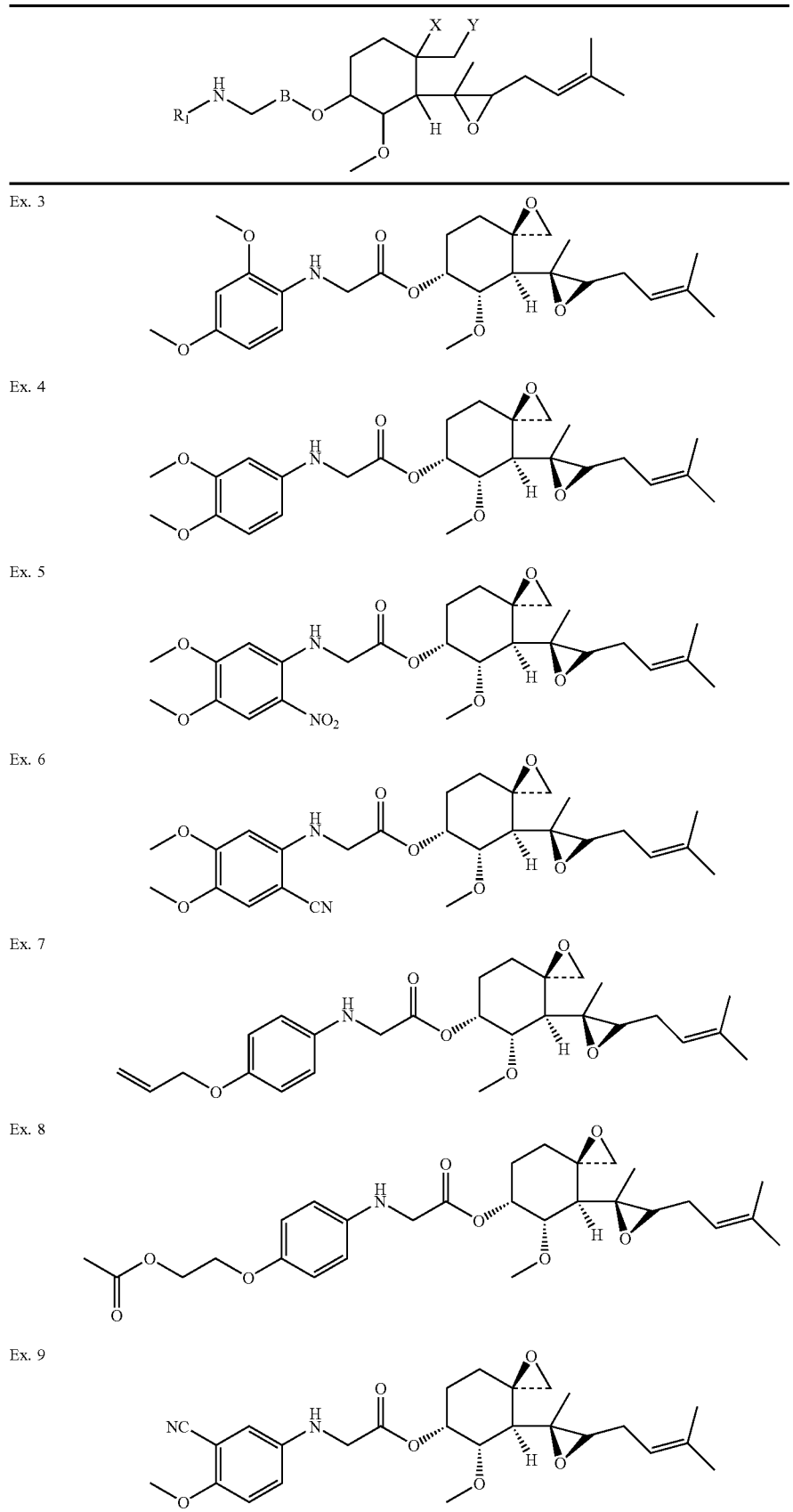

TABLE 1a-continued
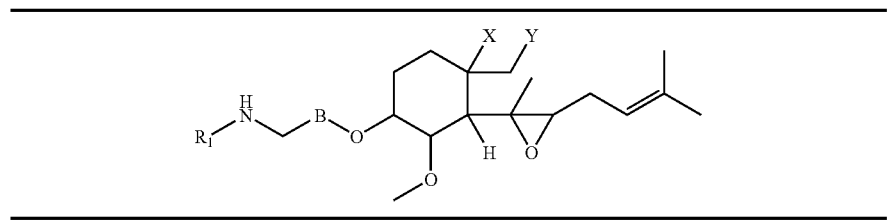
Ex. 10
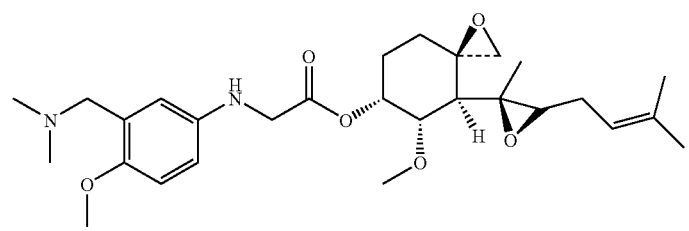
Ex. 11
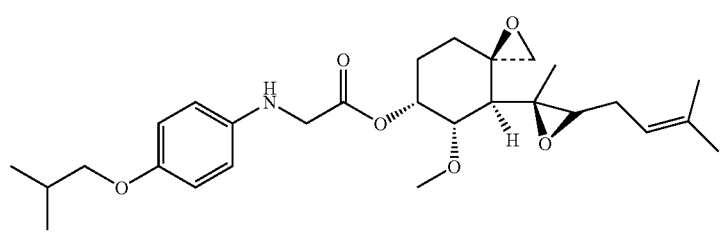
Ex. 12
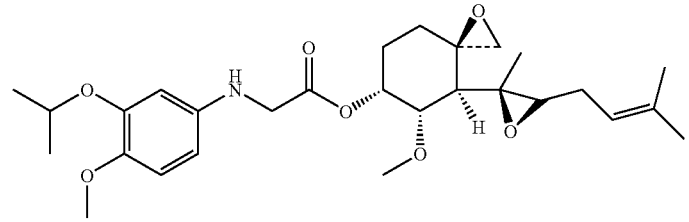
Ex. 13
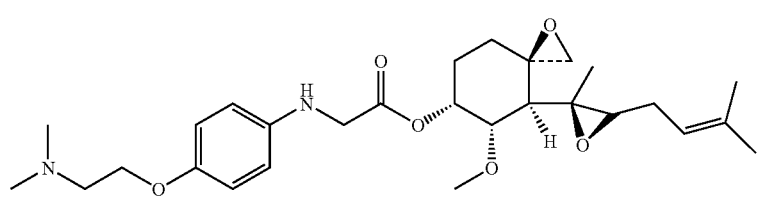
Ex. 14
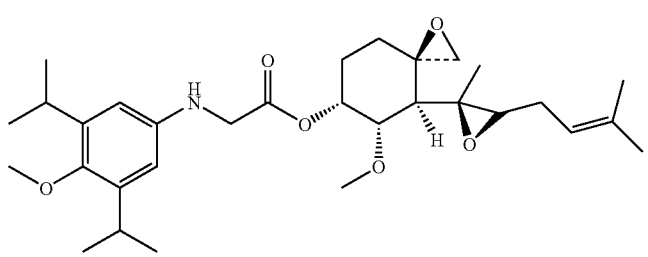
Ex. 15
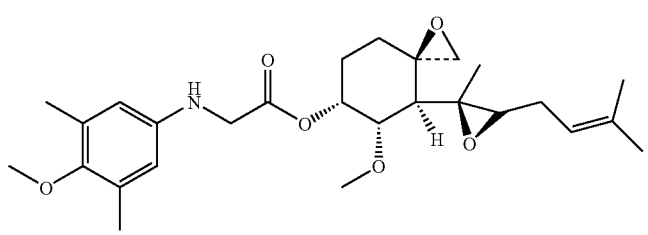

TABLE 1a-continued
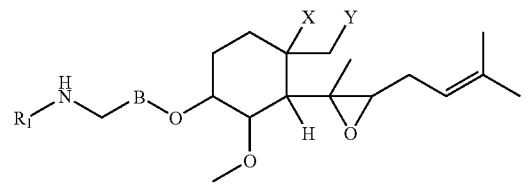
Ex. 16
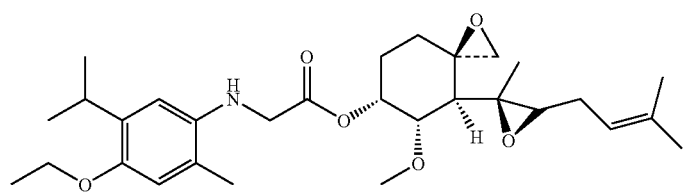
Ex. 17
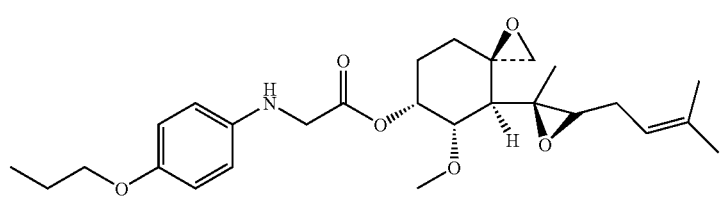
Ex. 18
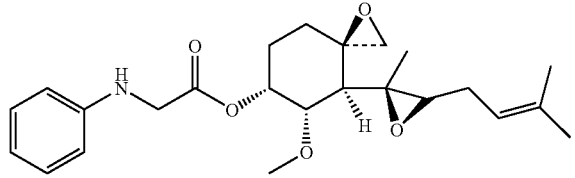
Ex. 19
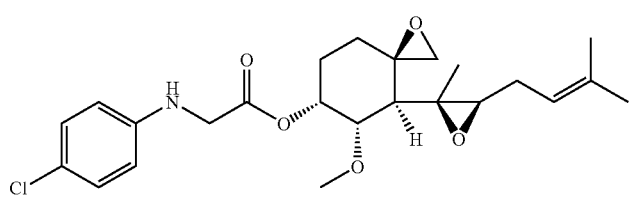
Ex. 20
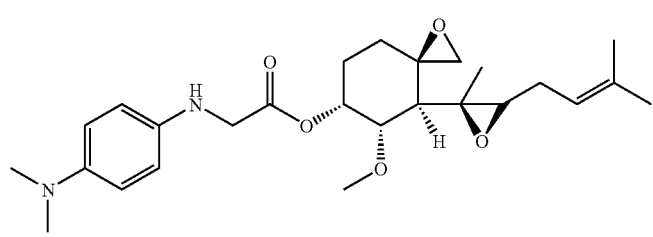

TABLE 1b
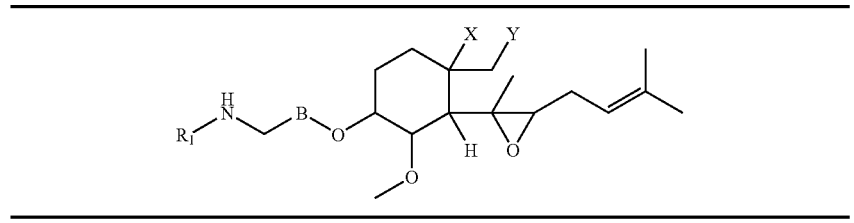
Ex. 21
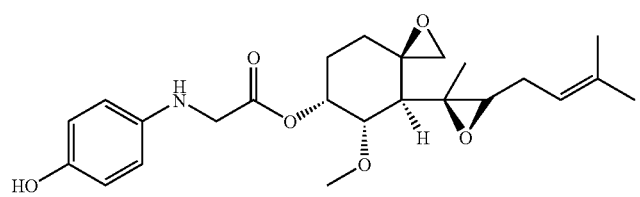
Ex. 22
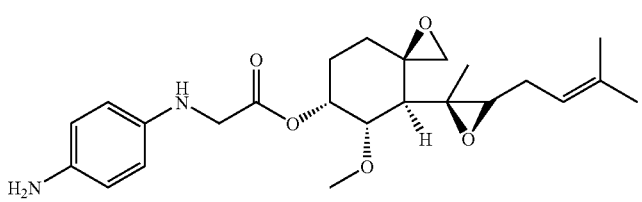
Ex. 23
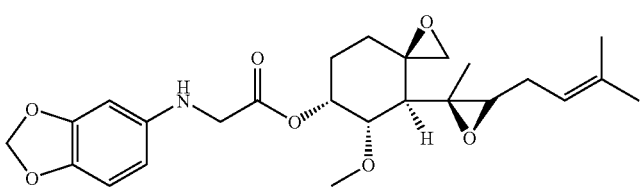
Ex. 24
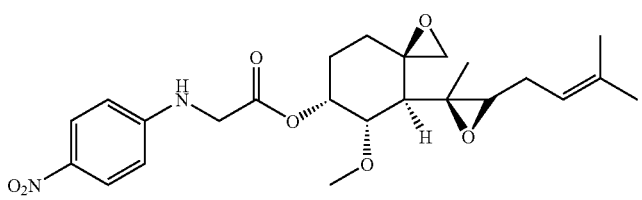
Ex. 25
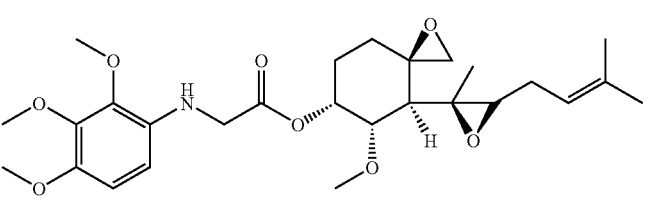
Ex. 26
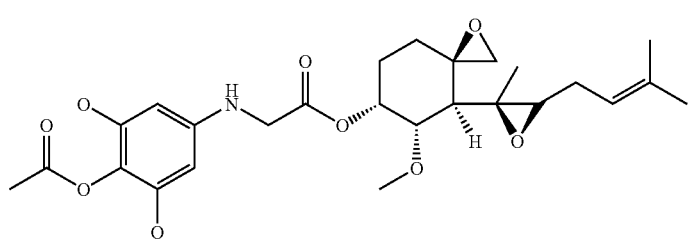

TABLE 1b-continued
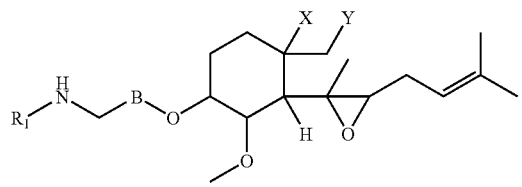
Ex. 27
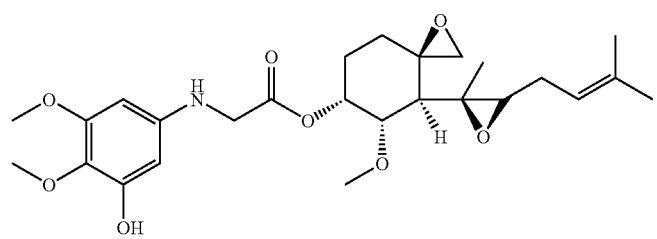
Ex. 28
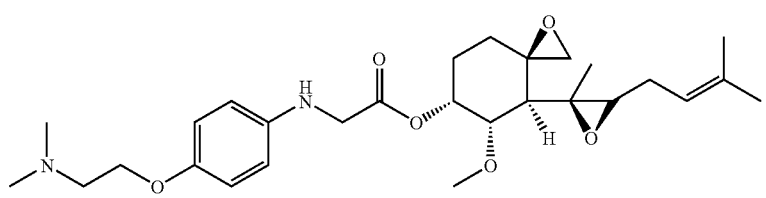
Ex. 29
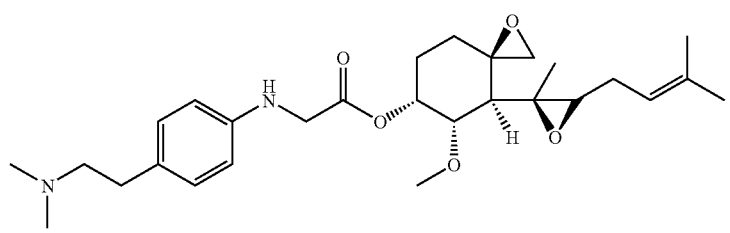
Ex. 30
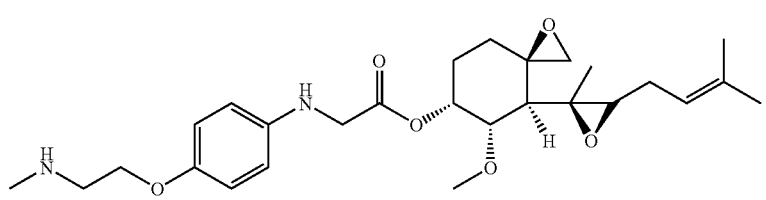
Ex. 31
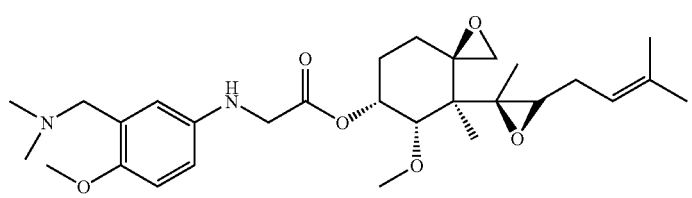
Ex. 32
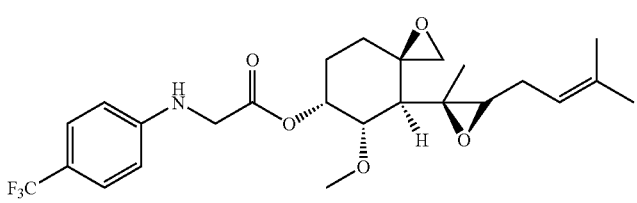

TABLE 1b-continued
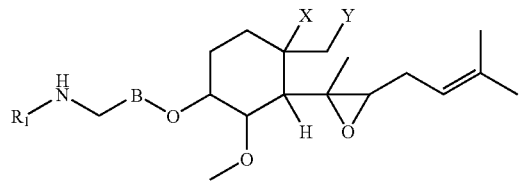
Ex. 33
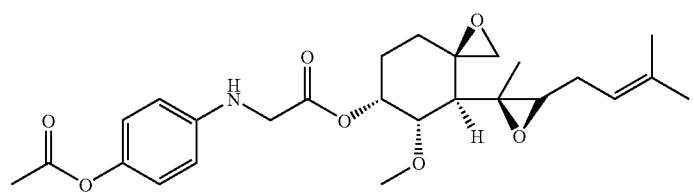
Ex. 34
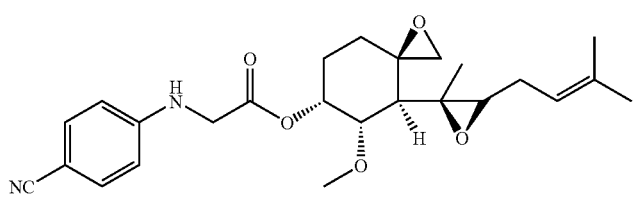
Ex. 35
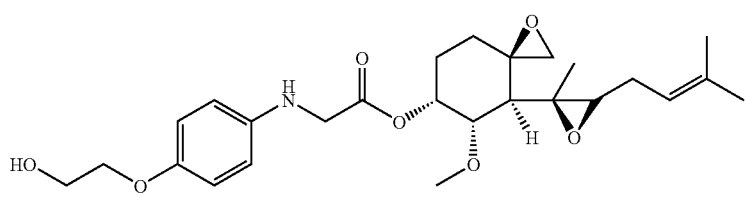
Ex. 36
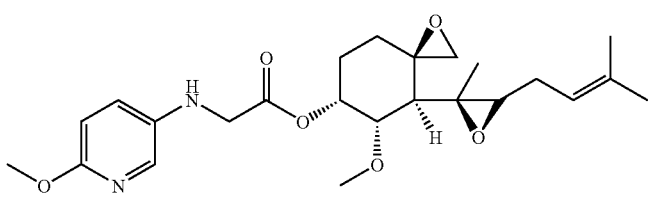
Ex. 37
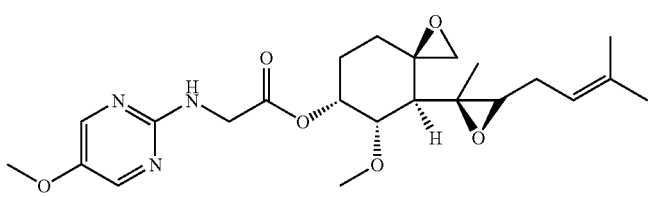
Ex. 38
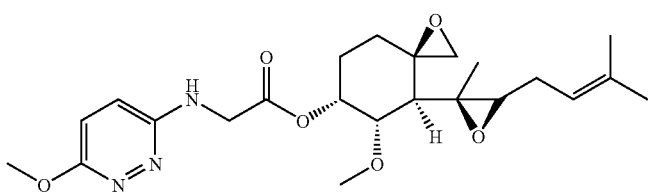

TABLE 1b-continued
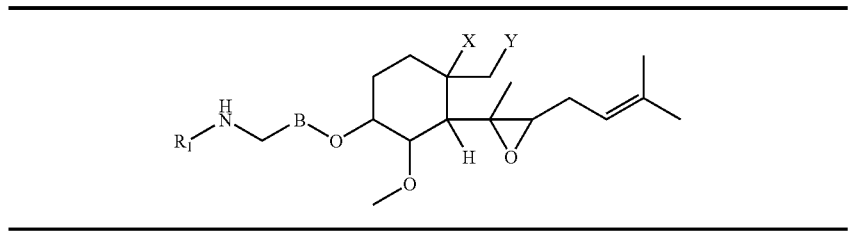
Ex. 39
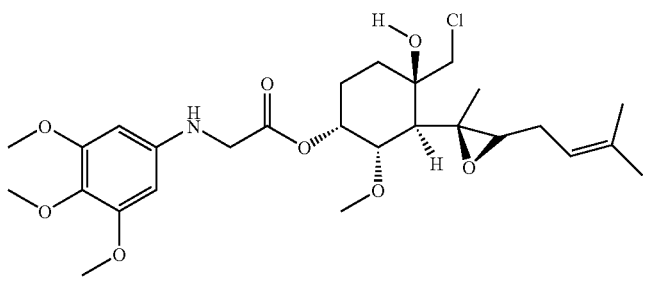
Ex. 40
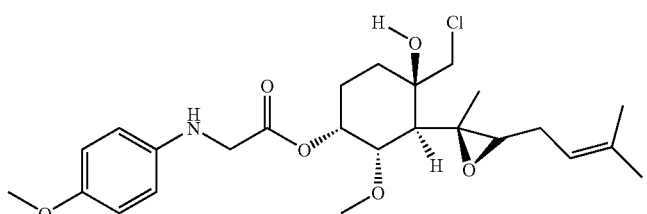
TABLE 1c
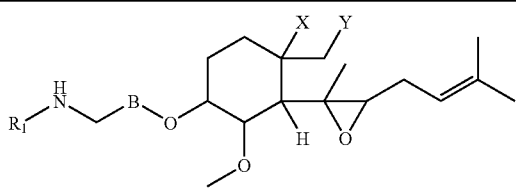
Ex. 41
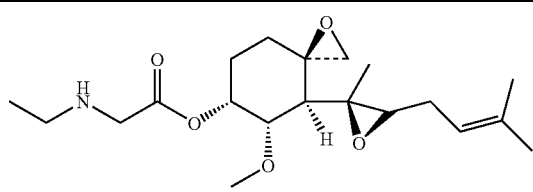
Ex. 42
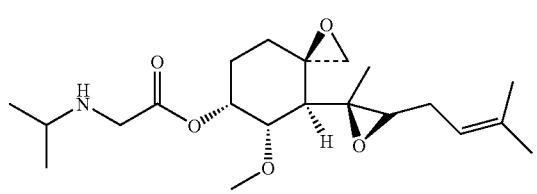
Ex. 43
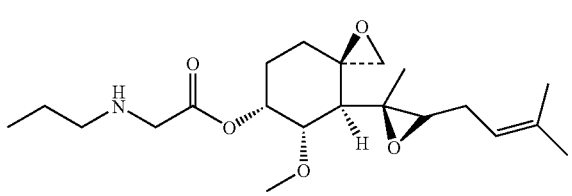

TABLE 1c-continued
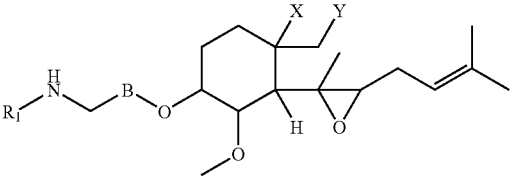
Ex. 44 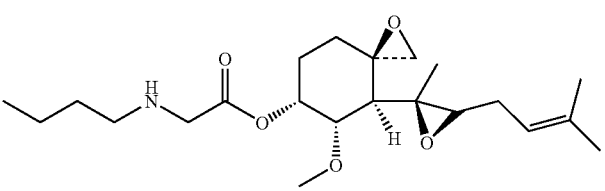
Ex. 45 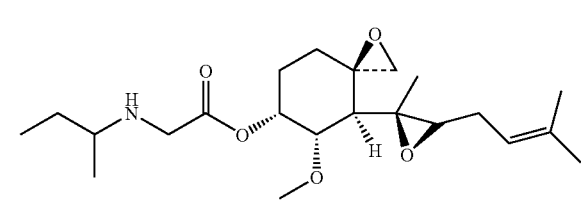
Ex. 46 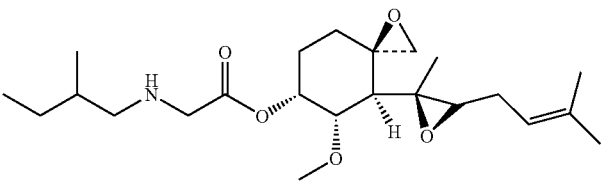
Ex. 47 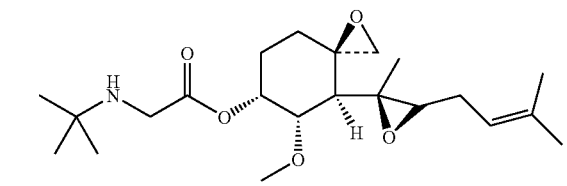
Ex. 48 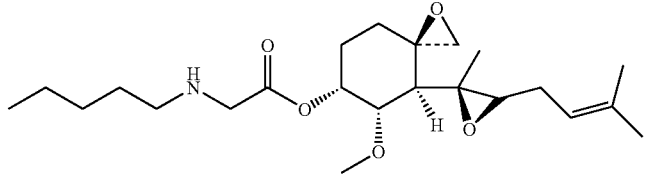
Ex. 49 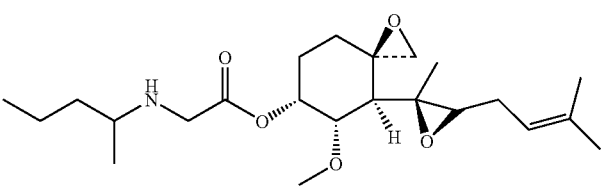
Ex. 50 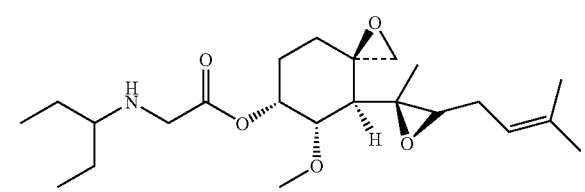

TABLE 1c-continued
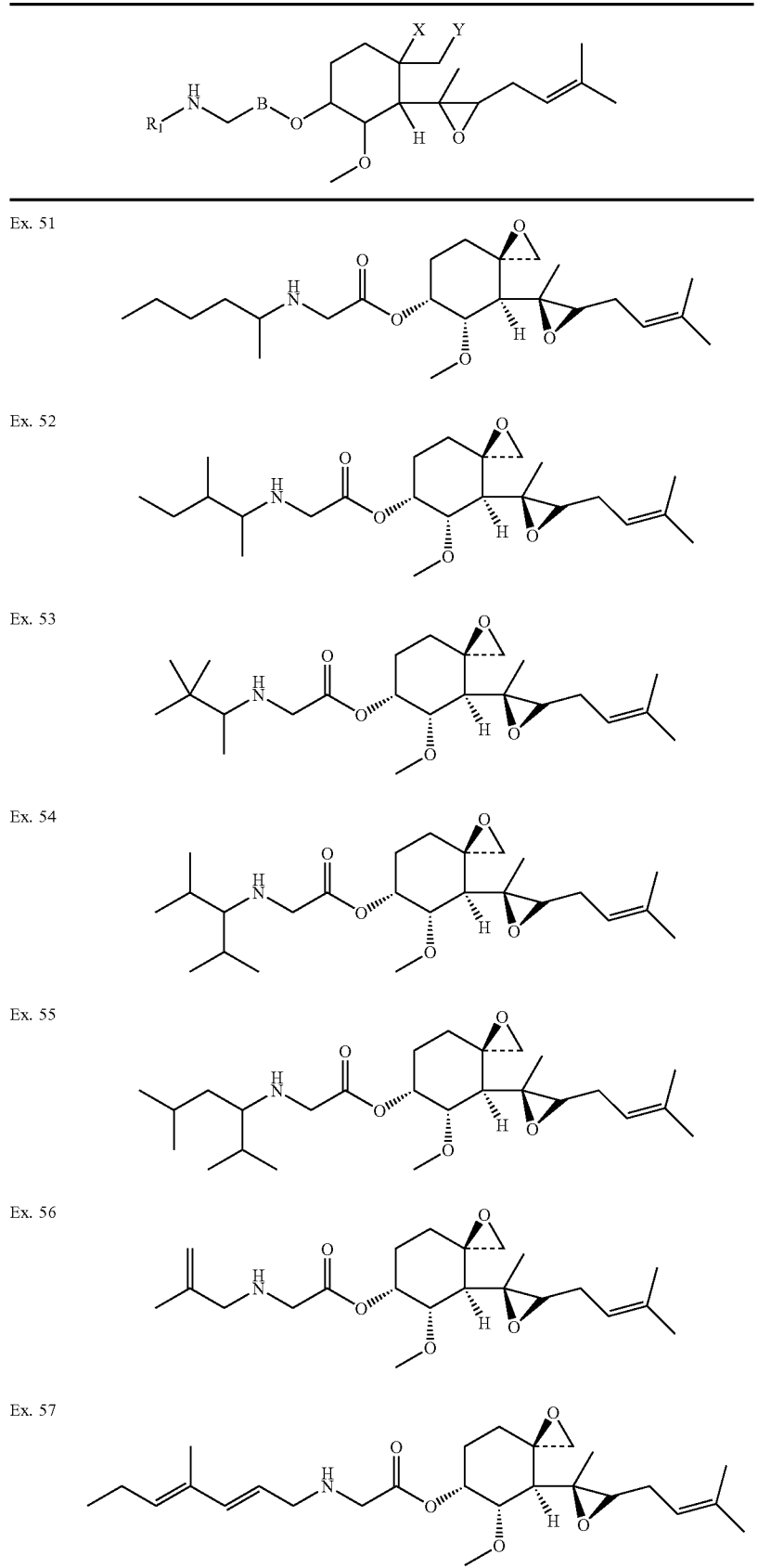
Ex. 51
Ex. 52
Ex. 53
Ex. 54
Ex. 55
Ex. 56
Ex. 57

TABLE 1c-continued
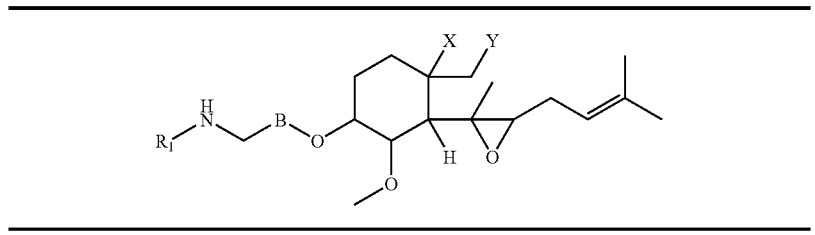
Ex. 58
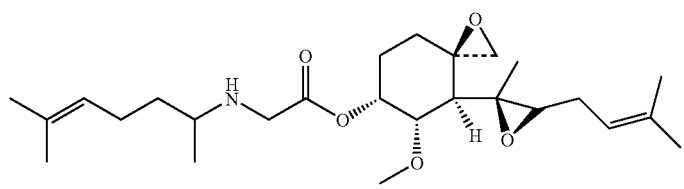
Ex. 59
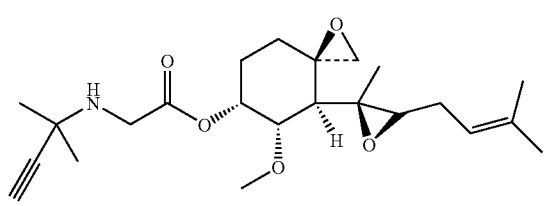
Ex. 60
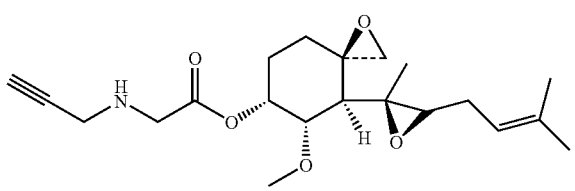
TABLE 1d
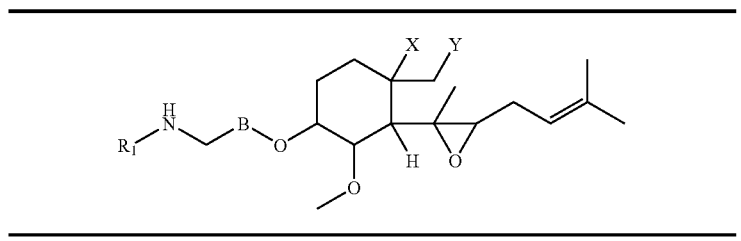
Ex. 61
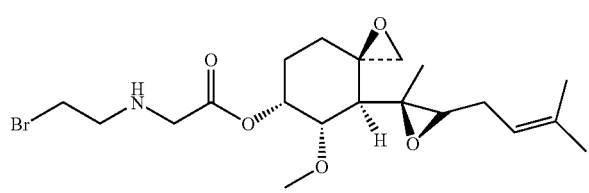
Ex. 62
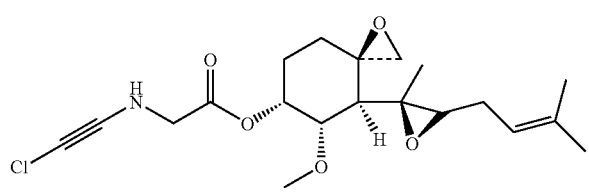

TABLE 1d-continued
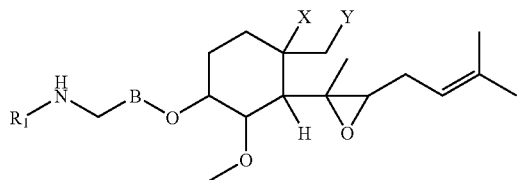
Ex. 63
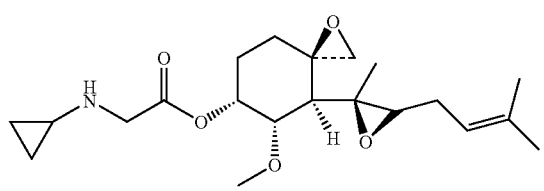
Ex. 64
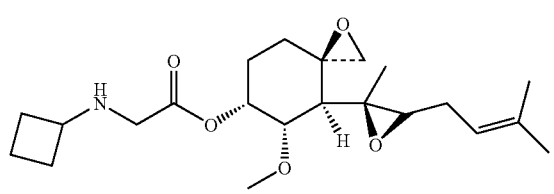
Ex. 65
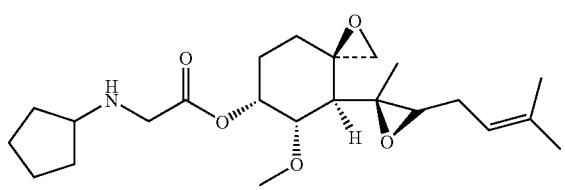
Ex. 66
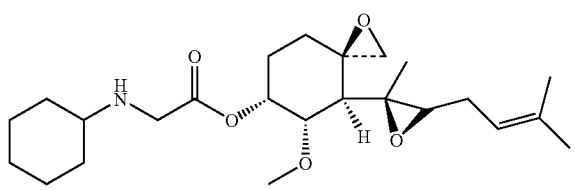
Ex. 67
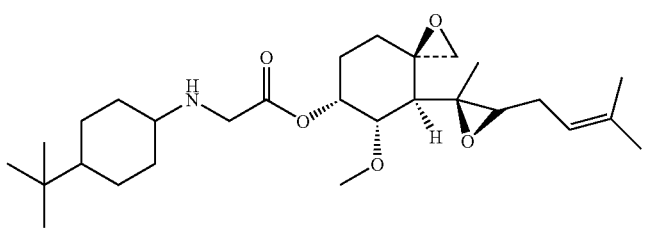
Ex. 68
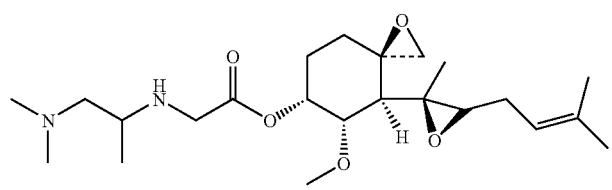
Ex. 69
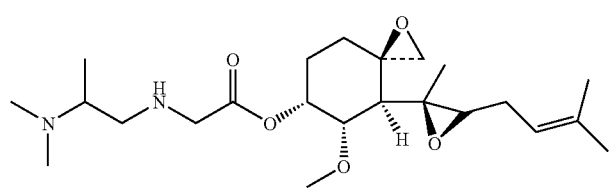

TABLE 1d-continued
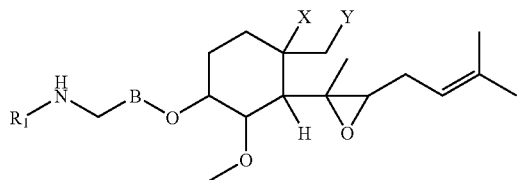
Ex. 70
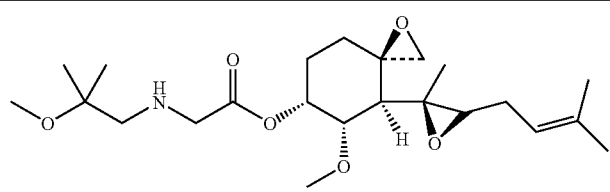
Ex. 71
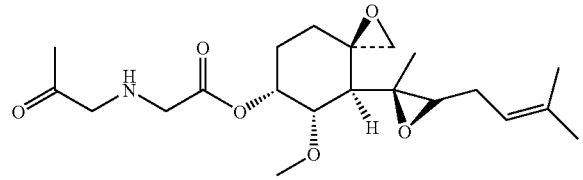
Ex. 72
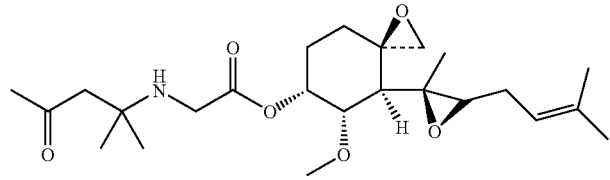
Ex. 73
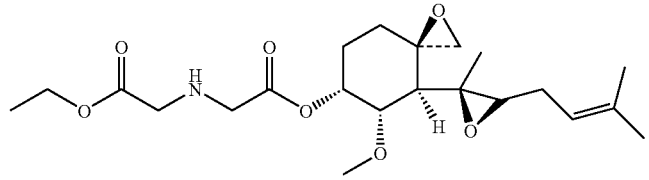
Ex. 74
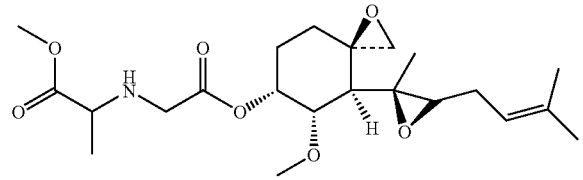
Ex. 75
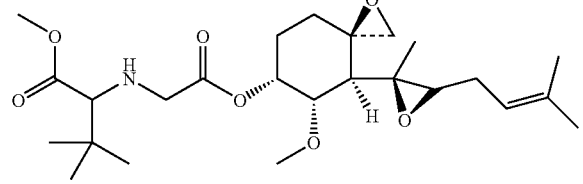
Ex. 76
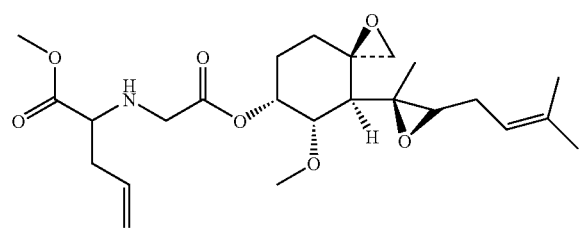

TABLE 1d-continued

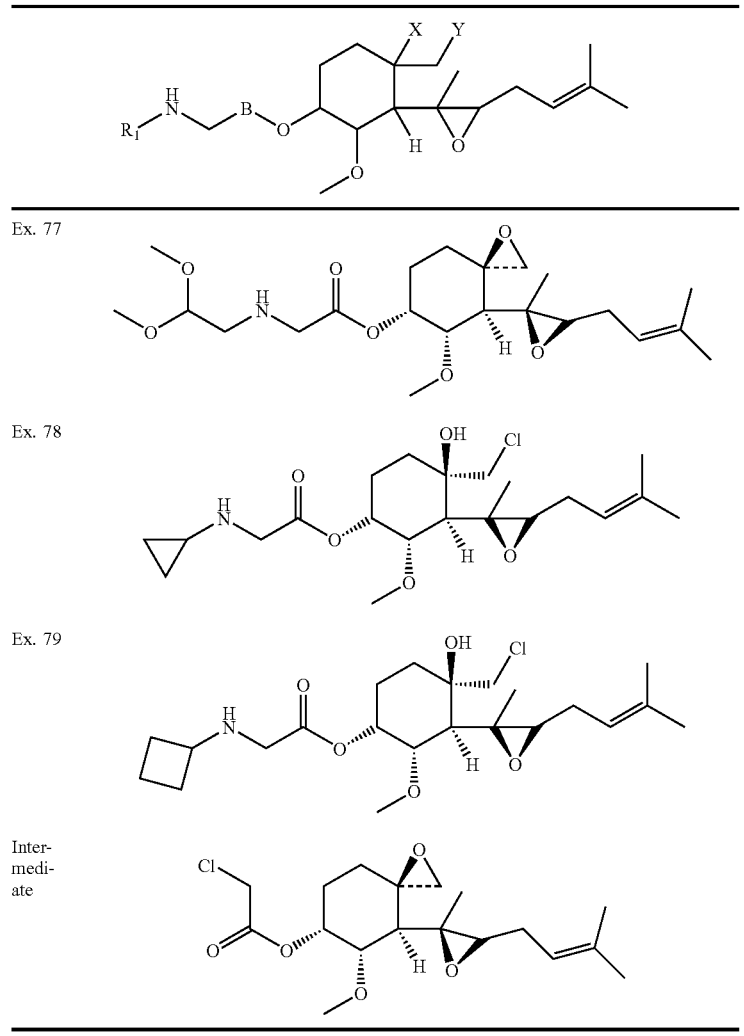

| | |
|---|---|
| Ex. 77 | |
| Ex. 78 | |
| Ex. 79 | |
| Intermediate | |

The fumagillol derivative of the present invention, represented by the formula I, may be used in a form of a pharmaceutically acceptable salt. In particular, an acid addition salt formed by a pharmaceutically acceptable free acid is usefully used. As the free acid, an inorganic acid and an organic acid may be used. Examples of the inorganic acid include hydrochloric acid, bromic acid, sulfuric acid and phosphoric acid. The organic acid is exemplified by citric acid, acetic acid, lactic acid, tartaric acid, maleic acid, umaric acid, gluconic acid, methansulfonic acid, glyconic acid, succinic acid, 4-toluenesulfonic acid, galacturonic acid, embonic acid, glutamic acid or aspartic acid.

Additionally, the present invention provides a method of preparing an acetyl fumagillol derivative and a pharmaceutically acceptable salt thereof, as represented by the following Reaction Scheme 1.

Specifically, the preparation method of the fumagillol derivative compound in which B is —(C=O)—, comprises the steps of:

(a) acylating a compound of the formula 2 with α-halocarboxylic acid derivative in the presence of a base, to give a compound of the formula 3; and (b) reacting the compound of the formula 3 with an amine compound of the formula 4, to prepare the fumagillol derivative represented by the formula 1a via substitution.

Reaction Scheme 1

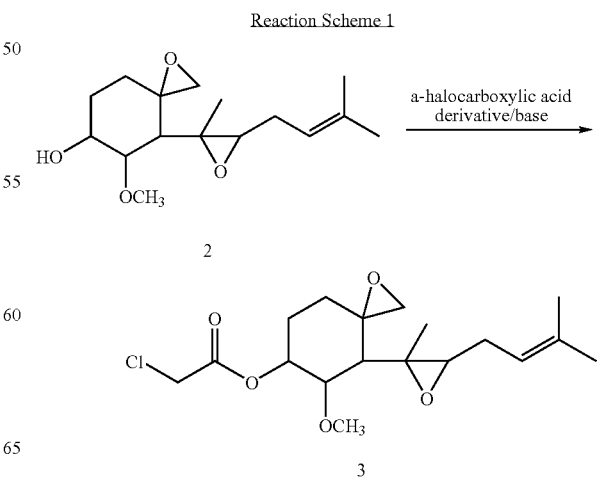

-continued

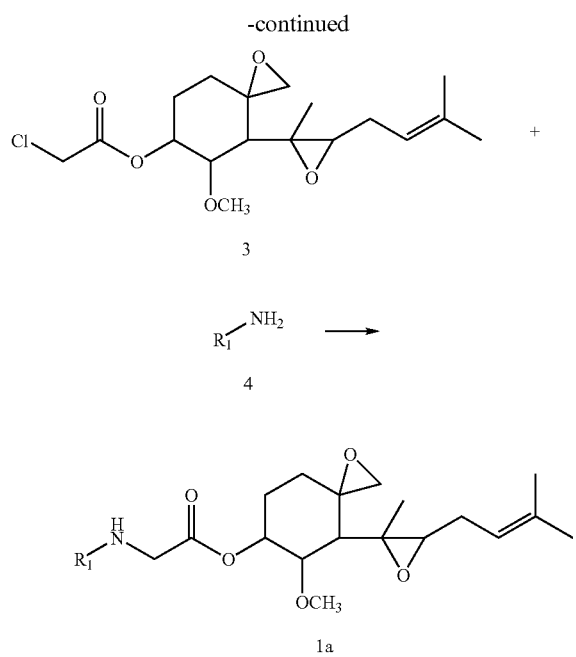

(wherein, R₁ is as defined above)

In the present invention, the prepared compound of the formula 1a is treated with an acid, or reacted with a salt in the presence of an acid catalyst, to perform an oxyrane ring-opening reaction, thereby yielding the fumagillol derivative represented by the formula 1b, as shown in the following Reaction Scheme 2:

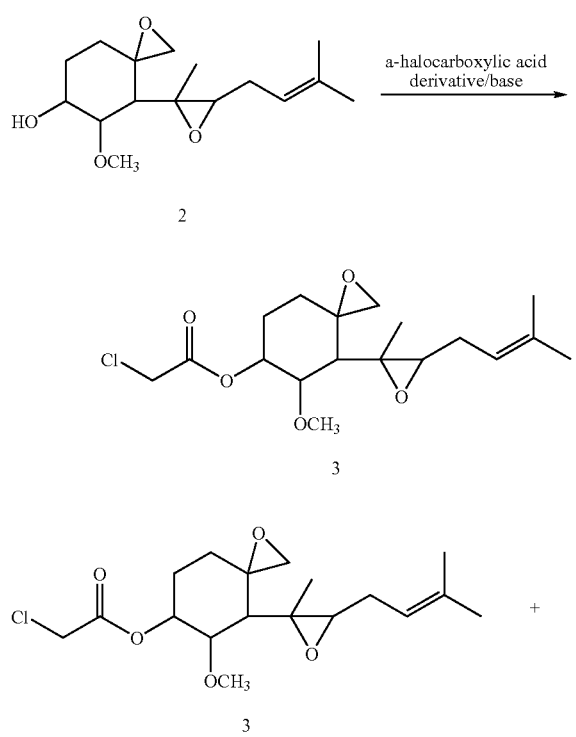

-continued

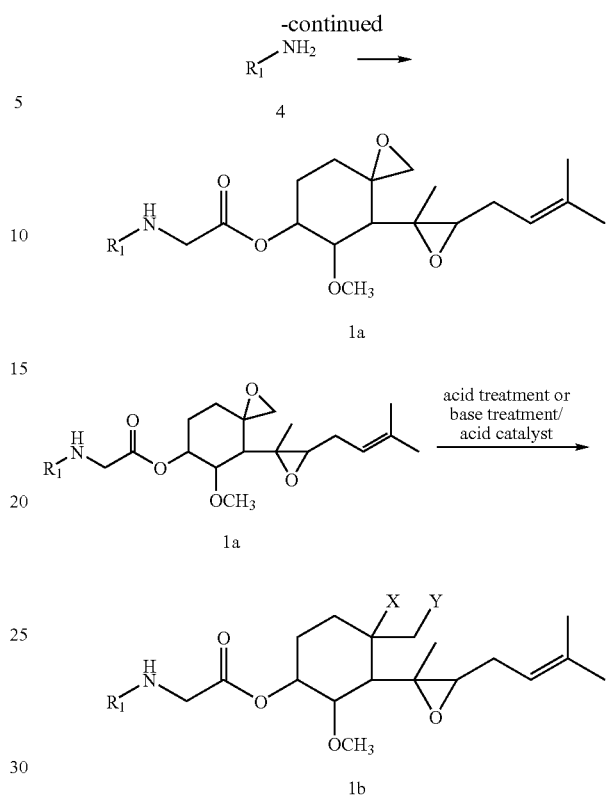

(wherein, $R_1$, X and Y are as defined above)

Below, a description will be given of each step.

(1) Acylation Step

The compound of the formula 2 as a starting material is acylated with α-halocarboxylic acid derivative having high reactivity, in the presence of the base, to give the compound of the formula 3, as seen in the following Reaction Scheme 3.

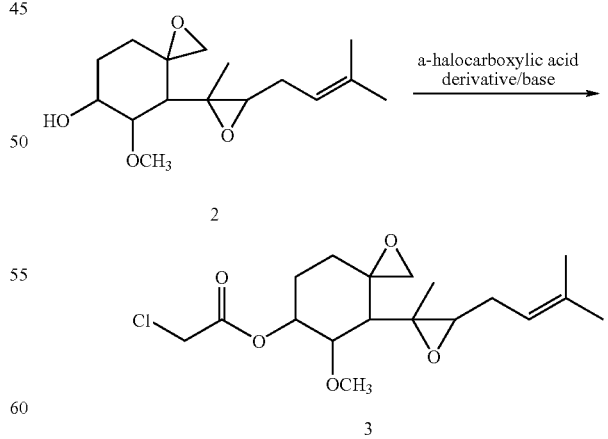

Specifically, the compound of the formula III is a fumagillol, which is a hydrolyzed product of fumagillin produced by microbial fermentation [Tarbell, D, S. et. al., *J. Am. Chem, Soc.*, 83, 3096 (1961)]81).

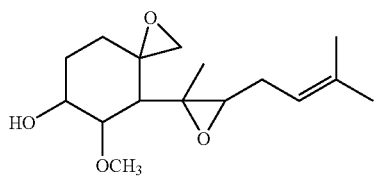

Formula III

The above α-halocarboxylic acid derivative is selected from among chloroacetyl chloride, chloroacetyl bromide, chloroacetyl iodide, and chloroacetyl fluoride, and used in the amount of 1–5 equivalents, preferably in 1–1.5 equivalents, based on the compound of the formula 2.

As for the base, an acid anhydride, a mixed anhydride or an acid chloride may be commonly used, and preferably, tertiary amines, such as triethylamine, diisopropylethyl amine, pyridine, dimethylamino pyridine, etc., are used in the amount of 1–10 equivalents. More preferably, 1–3 equivalents of triethylamine, or dimethylaminopyridine is used.

The solvent used for acylation is selected from the group consisting of dimethylformamide, dichloromethane, chloroform, diethylether, tetrahydrofuran, dioxane, acetonitrile, benzene and toluene. Preferably, dimethylformamide, dichloromethane or tetrahydrofuran is used.

As such, acylation is carried out at 0–50° C., preferably at 20–50° C.

2) Halogen-Amine Substitution Step

The compound of the formula 3, obtained from the previous acylation step, is reacted with the compound of the formula 4 as the amine derivative, to yield the compound of the formula 1a having a substituted amine compound, as seen in the following Reaction Scheme 4.

Reaction Scheme 4

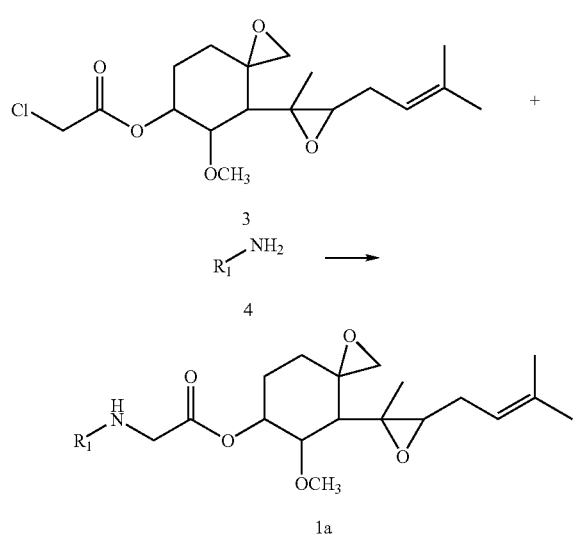

(wherein, $R_1$ is as defined above)

The aromatic compound of the formula 4, used in the above substitution reaction, is used in the amount of 1–10 equivalents, preferably 1–3 equivalents, based on the compound of the formula 3.

As for the amine compound, aliphatic or aromatic amine compound can be used. Such derivatives are specifically stated in the examples of the present invention.

The solvent used in this substitution reaction is selected from the group consisting of dimethylformamide, dichloromethane, chloroform, diethylether, tetrahydrofuran, dioxane, acetonitrile, benzene and toluene. It is preferred that dimethylformamide, dichloromethane or tetrahydrofuran is used.

The substitution reaction is performed at 0–100° C., preferably at 20–50° C.

3) Oxyrane Ring-Opening Step

The compound of the formula 1a, resulting from the above step, is treated with the acid, or reacted with the salt in the presence of the acid catalyst, to perform the oxyrane ring-opening reaction, thereby yielding the fumagillol derivative represented by the formula 1b, as in the following Reaction Scheme 5.

Reaction Scheme 5

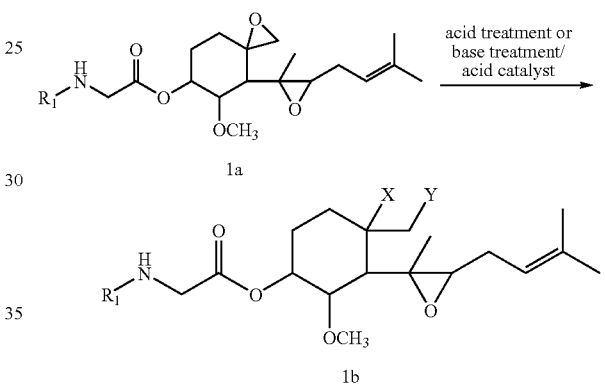

(wherein, $R_1$, X and $Y_4$ are as defined above)

Examples of the acid used in the ring-opening reaction include hydrochloric acid, bromic acid or iodic acid. The acid usable as the catalyst comprises acetic acid, sulfuric acid, para-toluene sulfonic acid, hydrochloric acid, phosphoric acid or nitric aicd. Of the acid catalysts, acetic acid or hydrochloric acid is preferably used.

The salt used in this reaction is selected from the group consisting of bromolithium, chlorolithium, sodium chloride, potassium chloride, potassium bromide, sodium bromide, potassium iodide, sodium iodide and lithium iodide. Preferably, chlorolithium, bromolithium, lithium iodide or sodium hydrogen carbonate.

Meanwhile, the preparation method of the compound in which B is —$CH_2$— is specifically shown in the following Reaction Scheme 6.

Reaction Scheme 6

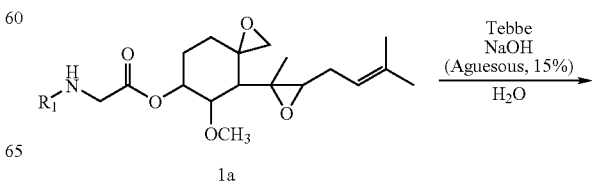

-continued

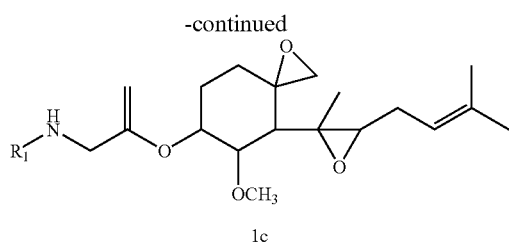

1c

Further, the present invention provides a pharmaceutical composition for angiogenesis inhibition, comprising the fumagillol derivative of the formula I or a pharmaceutically acceptable salt thereof as an effective ingredient.

In order to investigate activity of the fumagillol derivative on cell growth, proliferation inhibition activity was measured using HUVECs (human umbilical vein endothelial cells). As the result, it was found that the inventive fumagillol derivative has superior growth inhibition effect, up to 2000 times greater than TNP-470, a conventional angiogenesis inhibitory agent.

Therefore, it is expected that the fumagillol derivative of the formula I can strongly inhibit proliferation of vein endothelial cells, thus having excellent angiogenesis inhibitory effect. Such a fumagillol derivative can be usefully used for decreasing and inhibiting growth and metastasis of cancer as well as treating other various inflammatory diseases, including diabetic retinopathy, rheumatic arthritis and psoriasis. Hence, the fumagillol derivative is usable as a cancer metastasis inhibitor, or a therapeutic agent against cancer, rheumatic arthritis, psoriasis and diabetic retinopathy.

With a view to evaluating general toxicity of the compound of the formula I according to the present invention, experiments on acute toxicity were carried out using mice. As a result, it was found that the half lethal dose ($LD_{50}$) of each compound upon single oral administration was not less than 2 g/kg, whereby the compound was evaluated as a very safe compound.

The compound of the formula I according to the present invention may be formulated, upon clinical administration, as a pharmaceutical solid, semi-solid or liquid type formulation which is suitable for oral or parenteral administration by blending this compound with a pharmaceutically acceptable inert carrier.

The pharmaceutical composition of the present invention is formulated into dosage form for oral administration, for instance, tablet, troches, lozenge, water- or oil-soluble suspension, prepared powder or grain, emulsion, hard or soft capsule, syrup or elixir. For formulation of the tablet and capsule form, used are binders such as lactose, sacharose, sorbitol, mannitol, starch, amylopectin, cellulose or gelatin; vehicles such as dicalcium phosphate; disintegrating agents, such as corn starch or sweet-potato starch; and lubricants, such as magnesium stearate, calcium stearate, sodium stearylfumaric acid or polyethyleneglycol wax. In the case of capsule formulation, liquid carriers including fatty oil may be further included, in addition to the above materials.

Pharmaceutical preparations for parenteral administration comprise sterile aqueous solution, water-insoluble solvent, suspension, emulsion, and lyophilized agent. As the water-insoluble solvent and suspension, use may be made of vegetable oil such as propylene glycol, polyethylene glycol, olive oil, and injection ester, such as ethyl oleate.

In typical medical substances, effective doses of the compound of the formula I according to the present invention may range from 0.2 to 2.0 mg/kg, and they can be administered in a single dose or in divided daily doses. However, it should be understood by anyone skilled in the art that the amount of the active ingredient actually administered ought to be determined in light of various relevant factors including constitutional peculiarity and body weight of the individual subject, kinds and severity of diseases, properties of dosage form, properties of medicinal administration, and administration period or interval.

A better understanding of the present invention may be obtained in light of the following examples which are set forth to illustrate, but are not to be construed to limit the present invention.

EXAMPLE 1

Preparation of 6-O-(4-methoxyaniline)acetyl fumagillol

Step 1: (Acylation) Preparation of 6-O-chloroacetyl fumagillol

Fumagillol (500 mg) in dichloromethane (10 ml) was added with dimethylaminopyridine (432 mg) and chloroacetyl chloride (199 mg), and stirred at room temperature for 1 hour. The reaction was vacuum concentrated, to give the residue, which was then purified by silica gel column chromatography (ethyl acetate:n-hexane=1:4), yielding 270 mg of the title compound as a light yellow oil.

$^1$H-NMR (CDCl$_3$) δ: 5.76–5.74 (m, 1H), 5.22 (br t, 1H, J=7.3 Hz), 4.19 (s, 2H), 3.71 (dd, 1H, J=2.8, 11.1 Hz), 3.47 (s, 3H), 3.01 (d, 1H, J=4.3 Hz), 2.58 (t, 1H, J=6.4 Hz), 2.56 (d, 1H, J=4.3 Hz), 2.41–1.81 (m, 9H), 1.75 (s, 3H), 1.66 (s, 3H), 1.24 (s, 3H), 1.18–1.06 (m, 1H).

Step 2: (Substitution) Preparation of 6-O-(4-methoxyaniline)acetyl fumagillol

6-O-chloroacetyl fumagillol (160 mg), obtained from the above step 1, was dissolved in dimethylformamide (1 ml), to which 4-methoxyaniline (0.055 mg) was added. The mixture was further with K$_2$CO$_3$ (61.48 mg) and KI (73.84 mg) and stirred at 70° C. for 6 hours.

Thereafter, the resultant reaction was diluted with ethyl acetate (20 ml), and washed with saturated aqueous sodium hydrogen carbonate (5 ml) and saturated brine (5 ml). The organic layer was separated, dried over anhydrous magnesium sulfate and filtered. The obtained filtrate was vacuum concentrated to give the residue, which was purified by silica gel column chromatography (methanol:dichloromethane=1:10), yielding 112 mg of the title compound as a white solid.

$^1$H-NMR (CDCl$_3$) δ: 6.57 (s, 2H), 5.70–5.73 (m, 1H), 5.19 (br t, 1H, J=7.3 Hz), 4.21 (s, 2H), 3.86 (s, 3H), 3.72 (dd, 1H, J=2.9, 11.1 Hz), 3.45 (s, 3H), 3.01 (d, 1H, J=4.2 Hz), 2.56 (t, 1H, J=6.4 Hz), 2.54 (d, 1H, J=4.2 Hz), 2.43–1.83 (m, 6H), 1.78 (s, 3H) 1.63 (s, 3H) 1.25 (s, 3H) 1.19–1.03 (m, 1H).

EXAMPLE 2

Preparation of 6-O-(3,4,5-trimethoxyaniline)acetyl fumagillol

6-O-chloroacetyl fumagillol (166 mg), obtained from the above step 1 of the above example 1, was dissolved in dimethylformamide (1 ml), to which 3,4,5-trimethoxyaniline (0.079 mg) was added. Then, this mixture was further added with K$_2$CO$_3$ (63.78 mg) and KI (76.61 mg), and stirred at 70° C. for 6 hours.

The resultant reaction was diluted with ethyl acetate (20 ml), and washed with saturated aqueous sodium hydrogen carbonate (5 ml) and saturated brine (5 ml). The organic layer was separated, and dried over anhydrous magnesium sulfate and filtered. The obtained filtrate was vacuum concentrated to give the residue, which was purified by silica gel column chromatography (methanol:dichloromethane=1:10), yielding 136 mg of the title compound as a white solid.

$^1$H-NMR (CDCl$_3$) δ: 6.54 (s, 2H), 5.73–5.73 (m, 1H), 5.21 (br t, 1H, J=7.3 Hz), 4.21 (s, 2H), 3.89 (s, 9H), 3.72 (dd, 1H, J=2.9, 11.1 Hz), 3.44 (s, 3H), 3.01 (d, 1H, J=4.2 Hz), 2.58 (t, 1H, J=6.4 Hz), 2.54 (d, 1H, J=4.2 Hz), 2.43–1.83 (m, 6H), 1.75 (s, 3H) 1.67 (s, 3H) 1.23 (s, 3H) 1.15–1.04 (m, 1H).

EXAMPLE 3

Preparation of 6-O-(2,4-dimethoxyaniline)acetyl fumagillol

6-O-chloroacetyl fumagillol (168 mg), obtained from the above step 1 of the above example 1, was dissolved in dimethylformamide (1 ml), to which 2,4-dimethoxyaniline (0.072 mg) was added. Then, the mixture was further added with K$_2$CO$_3$ (64.54 mg) and KI (77.52 mg) and stirred at 70° C. for 6 hours.

The resultant reaction was diluted with ethyl acetate (20 ml), and washed with saturated aqueous sodium hydrogen carbonate (5 ml) and saturated brine (5 ml). The organic layer was separated, dried over anhydrous magnesium sulfate and filtered. The obtained filtrate was vacuum concentrated to give the residue, which was purified by silica gel column chromatography (methanol:dichloromethane=1:10), yielding 140 mg of the title compound as a white solid.

$^1$H-NMR (CDCl$_3$) δ: 6.57–6.48 (m, 3H), 5.73–5.71 (m, 1H), 5.24 (br t, 1H, J=7.2 Hz), 4.23 (s, 2H), 3.91 (s, 6H), 3.72 (dd, 1H, J=2.9, 11.0 Hz), 3.49 (s, 3H), 3.01 (d, 1H, J=4.3 Hz), 2.58 (t, 1H, J=6.4 Hz), 2.54 (d, 1H, J=4.3 Hz), 2.43–1.83 (m, 6H), 1.77 (s, 3H) 1.66 (s, 3H) 1.24 (s, 3H) 1.15–1.01 (m, 1H).

EXAMPLE 4

Preparation of 6-O-(3,4-dimethoxyaniline)acetyl fumagillol

6-O-chloroacetyl fumagillol (164 mg), obtained from the above step 1 of the above example 1, was dissolved in dimethylformamide (1 ml), to which 3,4-dimethoxyaniline (0.07 mg) was added. Then, the mixture was added with K$_2$CO$_3$ (63.01 mg) and KI (75.68 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The obtained filtrate was vacuum concentrated to give the residue, which was purified by silica gel column chromatography (methanol:dichloromethane=1:10), yielding 132 mg of the title compound as a colorless oil.

$^1$H-NMR (CDCl$_3$) δ: 6.54–6.47 (m, 3H), 5.73–5.69 (m, 1H), 5.21 (br t, 1H, J=7.2 Hz), 4.25 (s, 2H), 3.86 (s, 6H), 3.72 (dd, 1H, J=2.9, 11.1 Hz), 3.51 (s, 3H), 3.03 (d, 1H, J=4.2 Hz), 2.56 (t, 1H, J=6.4 Hz), 2.54 (d, 1H, J=4.2 Hz), 2.41–1.81 (m, 6H), 1.75 (s, 3H) 1.67 (s, 3H) 1.26 (s, 3H) 1.18–1.02 (m, 1H).

EXAMPLE 5

Preparation of 6-O-(3,4-dimethoxy-6-nitroaniline)acetyl fumagillol

6-O-chloroacetyl fumagillol (154 mg), obtained from the above step 1 of the above example 1, was dissolved in dimethylformamide (1 ml), to which 3,4-dimethoxy-6-nitroaniline (0.085 mg). Then, the mixture was added with K$_2$CO$_3$ (59.18 mg) and KI (71.08 mg) and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The obtained filtrate was vacuum concentrated to give the residue, which was purified by silica gel column chromatography (methanol:dichloromethane=1:10), yielding 161 mg of the title compound as a white solid.

$^1$H-NMR (CDCl$_3$) δ: 6.73–6.66 (m, 2H), 5.75–5.71 (m, 1H), 5.23 (br t, 1H, J=7.2 Hz), 4.27 (s, 2H), 3.93 (s, 6H), 3.72 (dd, 1H, J=2.9, 11.1 Hz), 3.49 (s, 3H), 3.01 (d, 1H, J=4.2 Hz), 2.58 (t, 1H, J=6.4 Hz), 2.54 (d, 1H, J=4.2 Hz), 2.43–1.83 (m, 6H), 1.75 (s, 3H) 1.64 (s, 3H) 1.25 (s, 3H) 1.18–1.03 (m, 1H).

EXAMPLE 6

Preparation of 6-O-(3,4-dimethoxy-6-cyanoaniline)acetyl fumagillol

6-O-chloroacetyl fumagillol (160 mg), obtained from the above step 1 of the above example 1, was dissolved in dimethylformamide (1 ml), to which 3,4-dimethoxy-6-cyanoaniline (0.079 mg) was added. The mixture was further added with K$_2$CO$_3$ (61.48 mg) and KI (73.84 mg), and stirred at 70° C. for 6 hours.

The resultant reaction was diluted with ethyl acetate (20 ml), and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 128 mg of the title compound as a white solid.

$^1$H-NMR (CDCl$_3$) δ: 6.77–6.64 (m, 2H), 5.73–5.70 (m, 1H) 5.21 (br t, 1H, J=7.2 Hz), 4.26 (s, 2H), 3.90 (s, 6H), 3.72 (dd, 1H, J=2.9, 11.1 Hz), 3.51 (s, 3H), 3.03 (d, 1H, J=4.1 Hz), 2.58 (t, 1H, J=6.4 Hz), 2.54 (d, 1H, J=4.1 Hz), 2.46–1.80 (m, 6H), 1.76 (s, 3H) 1.66 (s, 3H) 1.23 (s, 3H) 1.19–1.04 (m, 1H).

EXAMPLE 7

Preparation of 6-O-(4-allyloxyaniline)acetyl fumagillol

6-O-chloroacetyl fumagillol (165 mg), obtained from the above step 1 of the above example 1, was dissolved in dimethylformamide (1 ml), to which 4-allyloxyaniline (0.085 mg) was added. The mixture was further added with K$_2$CO$_3$ (63.40 mg) and KI (76.14 mg) and stirred at 70° C. for 7 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 151 mg of the title compound as a colorless oil.

$^1$H-NMR (CDCl$_3$) δ: 6.58–6.54 (m, 2H), 6.32–6.29 (m, 2H), 5.87–5.85 (m, 1H), 5.73–5.70 (m, 1H), 5.41–5.35 (m, 2H), 5.21 (br t, 1H, J=7.2 Hz), 4.61 (d, 2H, J=7.4 Hz), 4.26 (s, 2H), 3.72 (dd, 1H, J=2.9, 11.1 Hz), 3.51 (s, 3H), 3.03 (d, 1H, J=4.1 Hz), 2.58 (t, 1H, J=6.4 Hz), 2.54 (d, 1H, J=4.1 Hz), 2.46–1.80 (m, 6H), 1.76 (s, 3H) 1.66 (s, 3H) 1.23 (s, 3H) 1.19–1.04 (m, 1H).

EXAMPLE 8

Preparation of 6-O-(4-(2-acetoxyethoxy)aniline)acetyl fumagillol

6-O-chloroacetyl fumagillol (160 mg), obtained from the above step 1 of the above example 1, was dissolved in dimethylformamide (1 ml), to which 4-(2-acetoxyethoxy)aniline (0.08 mg) was added. Then, the mixture was further added with K$_2$CO$_3$ (61.48 mg) and KI (73.84 mg) and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 153 mg of the title compound as a colorless oil.

$^1$H-NMR (CDCl$_3$) δ: 6.54–6.52 (m, 2H), 6.38–6.34 (m, 2H), 5.73–5.70 (m, 1H), 5.21 (br t, 1H, J=7.2 Hz), 4.52 (t, 2H, J=7.0 Hz), 4.29 (t, 2H, J=7.0 Hz), 4.24 (s, 2H), 3.73 (dd, 1H, J=2.9, 11.1 Hz), 3.53 (s, 3H), 3.01 (d, 1H, J=4.3 Hz), 2.58 (t, 1H, J=6.4 Hz), 2.52 (d, 1H, J=4.3 Hz), 2.45–1.82 (m, 6H), 2.02 (s, 3H), 1.79 (s, 3H) 1.65 (s, 3H) 1.24 (s, 3H) 1.17–1.02 (m, 1H).

EXAMPLE 9

Preparation of 6-O-(3-cyano-4-methoxyaniline)acetyl fumagillol

6-O-chloroacetyl fumagillol (150 mg), obtained from the above step 1 of the above example 1, was dissolved in dimethylformamide (1 ml), to which 3-cyano-4-methoxyaniline (0.062 mg) was added. Then, the mixture was further added with K$_2$CO$_3$ (57.64 mg) and KI (69.22 mg) and stirred at 70° C. for 6 hours.

The resultant reaction was diluted with ethyl acetate (20 ml), and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 124 mg of the title compound as a white solid.

$^1$H-NMR (CDCl$_3$) δ: 6.77–6.64 (m, 3H), 5.73–5.70 (m, 1H), 5.21 (br t, 1H, J=7.2 Hz), 4.25 (s, 2H), 3.92 (s, 3H), 3.72 (dd, 1H, J=2.9, 11.1 Hz), 3.54 (s, 3H), 3.03 (d, 1H, J=4.1 Hz), 2.60 (t, 1H, J=6.4 Hz), 2.53 (d, 1H, J=4.1 Hz), 2.46–1.80 (m, 6H), 1.79 (s, 3H) 1.69 (s, 3H) 1.24 (s, 3H) 1.18–1.02 (m, 1H).

EXAMPLE 10

Preparation of 6-O-(3-(dimethylaminomethyl)-4-methoxyaniline)acetyl fumagillol 6-O-chloroacetyl fumagillol (153 mg), obtained from the above step 1 of the above example 1, was dissolved in dimethylformamide (1 ml), to which 3-(dimethylaminomethyl)-4-methoxyaniline (0.092 mg) was added. Then, the mixture was further added with K$_2$CO$_3$ (58.79 mg) and KI (70.61 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 161 mg of the title compound as a white solid.

$^1$H-NMR (CDCl$_3$) δ: 6.43–6.19 (m, 3H), 5.73–5.70 (m, 1H), 5.23 (br t, 1H, J=7.2 Hz), 4.23 (s, 2H), 3.93 (s, 3H), 3.74 (dd, 1H, J=2.9, 11.1 Hz), 3.66 (s, 2H), 3.52 (s, 3H), 3.00 (d, 1H, J=4.1 Hz), 2.58 (t, 1H, J=6.4 Hz), 2.52 (d, 1H, J=4.1 Hz), 2.46–1.80 (m, 6H), 2.26 (s, 6H), 1.78 (s, 3H) 1.66 (s, 3H) 1.25 (s, 3H) 1.16–1.04 (m, 1H).

EXAMPLE 11

Preparation of 6-O-(4-(2-methylpropoxyaniline)acetyl fumagillol

6-O-chloroacetyl fumagillol (152 mg), obtained from the above step 1 of the above example 1, was dissolved in dimethylformamide (1 ml), to which 4-(2-methylpropoxy)aniline (0.07 mg) was added. This mixture was further added with K$_2$CO$_3$ (58.41 mg) and KI (70.15 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 123 mg of the title compound as a white solid.

$^1$H-NMR (CDCl$_3$) δ: 6.59–6.55 (m, 2H), 6.37–6.33 (m, 2H), 5.74–5.71 (m, 1H), 5.25 (br t, 1H, J=7.2 Hz), 4.23 (s, 2H), 3.91 (d, 2H, J=6.5 Hz), 3.74 (dd, 1H, J=2.9, 11.1 Hz), 3.52 (s, 3H), 3.03 (d, 1H, J=4.1 Hz), 2.58 (t, 1H, J=6.4 Hz), 2.52 (d, 1H, J=4.1 Hz), 2.45–1.80 (m, 7H), 1.78 (s, 3H) 1.66 (s, 3H) 1.25 (s, 3H), 1.19 (d, 6H, J=6.1 Hz), 1.15–1.01 (m, 1H).

EXAMPLE 12

Preparation of 6-O-(3-isopropoxy-4-methoxyaniline)acetyl fumagillol

6-O-chloroacetyl fumagillol (161 mg), obtained from the above step 1 of the above example 1, was dissolved in dimethylformamide (1 ml), to which 3-(isopropoxy)-4-methoxyaniline (0.081 mg) was added. This mixture was added with K$_2$CO$_3$ (61.87 mg) and KI (74.3 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 151 mg of the title compound as a white solid.

$^1$H-NMR (CDCl$_3$) δ: 6.43–6.11 (m, 3H), 5.73–5.70 (m, 1H), 5.23 (br t, 1H, J=7.2 Hz), 4.23 (s, 2H), 4.11 (q, 1H, J=6.7 Hz), 3.93 (s, 3H), 3.74 (dd, 1H, J=2.9, 11.1 Hz), 3.52 (s, 3H), 3.00 (d, 1H, J=4.1 Hz), 2.58 (t, 1H, J=6.4 Hz), 2.52 (d, 1H, J=4.1 Hz), 2.46–1.80 (m, 6H), 1.78 (s, 3H) 1.66 (s, 3H), 1.40 (d, 6H, J=6.7 Hz), 1.25 (s, 3H) 1.16–1.04 (m, 1H).

EXAMPLE 13

Preparation of 6-O-(4-(N,N-dimethylethoxy)aniline)acetyl fumagillol

6-O-chloroacetyl fumagillol (154 mg), obtained from the above step 1 of the above example 1, was dissolved in dimethylformamide (1 ml), to which 4-(N,N-dimethylethoxy)aniline (0.077 mg) was added. This mixture was further added with K$_2$CO$_3$ (59.18 mg) and KI (71.08 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 158 mg of the title compound as a white solid.

$^1$H-NMR (CDCl$_3$) δ: 6.61–6.57 (m, 2H), 6.39–6.35 (m, 2H), 5.74–5.70 (m, 1H), 5.26 (br t, 1H, J=7.2 Hz), 4.23 (s, 2H), 4.03 (t, 2H, J=6.8 Hz), 3.75 (dd, 1H, J=2.9, 11.1 Hz), 3.52 (s, 3H), 3.05 (d, 1H, J=4.1 Hz), 2.57 (t, 1H, J=6.4 Hz), 2.79 (t, 2H, J=6.8 Hz), 2.59 (s, 6H), 2.50 (d, 1H, J=4.1 Hz), 2.45–1.80 (m, 6H), 1.77 (s, 3H) 1.65 (s, 3H) 1.26 (s, 3H), 1.17–1.02 (m, 1H).

EXAMPLE 14

Preparation of 6-O-(3,5-diisopropyl-4-methoxyaniline)acetyl fumagillol

6-O-chloroacetyl fumagillol (160 mg), obtained from the above step 1 of the above example 1, was dissolved in dimethylformamide (1 ml), to which 3,5-diisopropyl-4-methoxyaniline (0.092 mg) was added. This mixture was further added with K$_2$CO$_3$ (61.48 mg) and KI (73.84 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The obtained filtrate was vacuum concentrated to give the residue, which was purified by silica gel column chromatography (methanol:dichloromethane=1:10), yielding 171 mg of the title compound as a white solid.

$^1$H-NMR (CDCl$_3$) δ: 6.58–6.54 (m, 2H), 5.74–5.71 (m, 1H), 5.25 (br t, 1H, J=7.2 Hz), 4.23 (s, 2H), 3.91 (s, 3H), 3.74 (dd, 1H, J=2.9, 11.1 Hz), 3.52 (s, 3H), 3.19 (q, 2H, J=6.3 Hz), 3.03 (d, 1H, J=4.1 Hz), 2.58 (t, 1H, J=6.4 Hz), 2.52 (d, 1H, J=4.1 Hz), 2.45–1.80 (m, 6H), 1.78 (s, 3H) 1.69 (s, 3H), 1.32 (d, 12H, J=6.3 Hz), 1.25 (s, 3H), 1.18–1.00 (m, 1H).

EXAMPLE 15

Preparation of 6-O-(3,5-dimethyl-4-methoxyaniline)acetyl fumagillol

6-O-chloroacetyl fumagillol (155 mg), obtained from the above step 1 of the above example 1, was dissolved in dimethylformamide (1 ml), to which 3,5-dimethyl-4-methoxyaniline (0.065 mg) was added. This mixture was further added with K$_2$CO$_3$ (59.56 mg) and KI (71.53 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 145 mg of the title compound as a white solid.

$^1$H-NMR (CDCl$_3$) δ: 6.56–6.51 (m, 2H), 5.75–5.72 (m, 1H), 5.27 (br t, 1H, J=7.2 Hz), 4.25 (s, 2H), 3.93 (s, 3H), 3.72 (dd, 1H, J=2.9, 11.1 Hz), 3.55 (s, 3H), 3.04 (d, 1H, J=4.1 Hz), 2.56 (t, 1H, J=6.4 Hz), 2.50 (d, 1H, J=4.1 Hz), 2.45–1.80 (m, 12H), 1.78 (s, 3H) 1.69 (s, 3H), 1.25 (s, 3H), 1.18–1.00 (m, 1H).

EXAMPLE 16

Preparation of 6-O-(3-isopropyl-4-ethoxy-6-methylaniline)acetyl fumagillol

6-O-chloroacetyl fumagillol (158 mg), obtained from the above step 1 of the above example 1, was dissolved in dimethylformamide (1 ml), to which 3-isopropyl-4-ethoxy-6-methylaniline (0.101 mg) was added. This mixture was added with K$_2$CO$_3$ (60.71 mg) and KI (72.91 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 166 mg of the title compound as a white solid.

$^1$H-NMR (CDCl$_3$) δ: 6.54–6.51 (m, 2H), 5.75–5.72 (m, 1H), 5.27 (br t, 1H, J=7.2 Hz), 4.21 (s, 2H), 3.97 (q, 2H, J=6.2 Hz), 3.74 (dd, 1H, J=2.9, 11.1 Hz), 3.52 (s, 3H), 3.14 (q, 1H, J=6.5 Hz), 3.03 (d, 1H, J=4.1 Hz), 2.58 (t, 1H, J=6.4 Hz), 2.52 (d, 1H, J=4.1 Hz), 2.45–1.80 (m, 9H), 1.78 (s, 3H) 1.69 (s, 3H), 1.35 (t, 3H, J=6.2 Hz), 1.28 (d, 6H, J=6.5 Hz), 1.25 (s, 3H), 1.18–1.00 (m, 1H).

EXAMPLE 17

Preparation of 6-O-(4-propyloxyaniline)acetyl fumagillol

6-O-chloroacetyl fumagillol (160 mg), obtained from the above step 1 of the above example 1, was dissolved in dimethylformamide (1 ml), to which 4-propyloxyaniline (0.084 mg) was added. This mixture was added with K$_2$CO3 (61.48 mg) and KI (73.84 mg), and stirred at 70° C. for 6 hours.

The resultant reaction was diluted with ethyl acetate (20 ml), and washed with saturated aqueous sodium hydrogen carbonate (5 ml) and saturated brine (5 ml). The separated organic layer was dried over anhydrous magnesium sulfate and filtered. The filtrate was vacuum concentrated to give the residue, which was purified by silica gel column chromatography (methanol:dichloromethane=1:10), yielding 105 mg of the title compound as a white solid.

$^1$H-NMR (CDCl$_3$) δ: 6.63–6.58 (m, 2H), 6.40–6.36 (m, 2H), 5.74–5.71 (m, 1H), 5.25 (br t, 1H, J=7.2 Hz), 4.23 (s, 2H), 3.95 (t, 2H, J=6.8 Hz), 3.74 (dd, 1H, J=2.9, 11.1 Hz), 3.55 (s, 3H), 3.01 (d, 1H, J=4.1 Hz), 2.58 (t, 1H, J=6.4 Hz), 2.52 (d, 1H, J=4.1 Hz), 2.45–1.82 (m, 6H), 1.77–1.74 (m, 5H) 1.68 (s, 3H) 1.26 (s, 3H), 1.15–1.01 (m, 4H).

EXAMPLE 18

Preparation of 6-O-(aniline)acetyl fumagillol

6-O-chloroacetyl fumagillol (157 mg), obtained from the above step 1 of the above example 1, was dissolved in dimethylformamide (1 ml), to which aniline (0.04 mg) was added. This mixture was added with K$_2$CO$_3$ (60.33 mg) and KI (72.46 mg), and stirred at 70° C. for 6 hours.

The resultant reaction was diluted with ethyl acetate (20 ml), and washed with saturated aqueous sodium hydrogen carbonate (5 ml) and saturated brine (5 ml). The organic layer was dried over anhydrous magnesium sulfate and filtered. The obtained filtrate was vacuum concentrated to give the residue, which was purified by silica gel column chromatography (methanol:dichloromethane=1:10), yielding 118 mg of the title compound as a white solid.

$^1$H-NMR (CDCl$_3$) δ: 7.66–7.14 (m, 5H), 5.75–5.71 (m, 1H), 5.20 (br t, 1H, J=7.3 Hz), 4.18 (s, 2H), 3.72 (dd, 1H, J=2.8, 11.1 Hz), 3.45 (s, 3H), 3.00 (d, 1H, J=4.3 Hz), 2.59 (t, 1H, J=6.4 Hz), 2.58 (d, 1H, J=4.3 Hz), 2.41–1.81 (m, 6H), 1.78 (s, 3H) 1.66 (s, 3H), 1.26 (s, 3H), 1.17–1.04 (m, 1H).

EXAMPLES 19–38

The fumagillol derivatives represented by the formula I were prepared in the same manner as in the above example 1, except that aromatic compounds were changed. The results are given in Table 2, below.

TABLE 2

| Ex. No. | Fumagillol Derivative | Aromatic Compound |
|---|---|---|
| 19 | 6-O-(4-chloroaniline)acetyl fumagillol | 4-chloroaniline |
| 20 | 6-O-(4-dimethylaminoaniline)acetyl fumagillol | 4-dimethylaminoaniline |
| 21 | 6-O-(4-hydroxyaniline)acetyl fumagillol | 4-hydroxyaniline |
| 22 | 6-O-(4-aminoaniline)acetyl fumagillol | 4-aminoaniline |
| 23 | 6-O-(3,4-methylenedioxyaniline)acetyl fumagillol | 3,4-methylenedioxyaniline |
| 24 | 6-O-(4-nitroaniline)acetyl fumagillol | 4-nitroaniline |
| 25 | 6-O-(2,3,4-trimethoxyaniline)acetyl fumagillol | 2,3,4-trimethoxyaniline |
| 26 | 6-O-(4-acetoxy-3,5-dimethoxyaniline)acetyl fumagillol | 4-acetoxy-3,5-dimethoxyaniline |
| 27 | 6-O-(3,4-dimethoxy-4-hydroxyaniline)acetyl fumagillol | 3,4-dimethoxy-4-hydroxyaniline |
| 28 | 6-O-(4-dimethylaminoethoxyaniline)acetyl fumagillol | 4-dimethylaminoethoxyaniline |
| 29 | 6-O-(4-ethylamino)acetyl fumagillol | 4-ethylamino |
| 30 | 6-O-(4-ethylaminoaniline)acetyl fumagillol | 4-ethylaminoaniline |
| 31 | 6-O-(3-dimethylaminomethyl-4-methoxyaniline)acetyl fumagillol | 3-dimethylaminomethyl-4-methoxyaniline |
| 32 | 6-O-(4-trifluoromethylaniline)acetyl fumagillol | 4-trifluoromethylaniline |
| 33 | 6-O-(4-acetoxyaniline)acetyl fumagillol | 4-acetoxyaniline |
| 34 | 6-O-(4-cyanoaniline)acetyl fumagillol | 4-cyanoaniline |
| 35 | 6-O-(4-hydroxyethoxyaniline)acetyl fumagillol | 4-hydroxyethoxyaniline |
| 36 | 6-O-(5-amino-2-methoxypyridine)acetyl fumagillol | 5-amino-2-methoxypyridine |
| 37 | 6-O-(5-methoxypyrimidine-2-amino)acetyl fumagillol | 5-methoxypyrimidine-2-amino |
| 38 | 6-O-(3-methoxy-6-aminopyridazine)acetyl fumagillol | 3-methoxy-6-aminopyridazine |

Each of the fumagillol derivatives, obtained from the above examples 1 and 2, was treated with an acid, or reacted with a salt in the presence of an acid catalyst, to perform an oxyrane ring-opening reaction.

EXAMPLE 39

Preparation of 4-((4-methoxyaniline)acetyl)oxy-2-(1,2-epoxy-1,5-dimethyl-4-hexenyl)-3-methoxy-1-chloromethyl-1-cyclohexanol 6-O-(4-methoxyaniline)acetyl fumagillol (100 mg), obtained from the above example 1, was dissolved in tetrahydrofuran (10 ml), to which chlorolithium (48 mg) and acetic acid (0.12 ml) were added. This mixture was stirred at 30° C. for 36 hours. The resultant reaction was added with water (10 ml) and ethyl acetate (100 ml). The organic layer was separated, washed with saturated brine (10 ml), dried over anhydrous magnesium sulfate and filtered, followed by distilling off the solvent under reduced pressure. Then, thusly obtained residue was purified by silica gel column chromatography (ethyl acetate:n-hexane=1:2), to give 85 mg of the title compound as a white solid.

$^1$H-NMR (CDCl$_3$) δ: 6.57 (s, 2H), 5.70–5.73 (m, 1H), 5.19 (br t, 1H, J=7.3 Hz), 4.21 (s, 2H), 3.86 (3s, 9H), 3.72 (dd, 1H, J=2.6, 11.1 Hz), 3.45 (s, 3H), 3.01 (d, 1H, J=4.2

Hz), 2.56 (t, 1H, J=6.4 Hz), 2.54 (d, 1H, J=4.2 Hz), 2.43–1.83 (m, 6H), 1.78 (s, 3H) 1.63 (s, 3H) 1.25 (s, 3H) 1.19–1.03 (m, 1H).

EXAMPLE 40

Preparation of 4-((3,4,5-trimethoxyaniline)acetyl)oxy-2-(1,2-epoxy-1,5-dimethyl-4-hexenyl)-3-methoxy-1-chloromethyl-1-cyclohexanol 6-O-(3,4,5-trimethoxyaniline)acetyl fumagillol (100 mg), obtained from the above example 2, in tetrahydrofuran (10 ml), was added with hydrochloric acid (0.14 ml) and stirred for 32 hours. This mixture was added with water (10 ml) and ethyl acetate (100 ml). The organic layer was separated, washed with saturated brine (10 ml), dried over anhydrous magnesium sulfate and filtered. Then, the solvent was distilled off under reduced pressure, to give the residue, which was purified by silica gel column chromatography (ethyl acetate:n-hexane=1:2), yielding 72 mg of the title compound as a white solid.

$^1$H-NMR (CDCl$_3$) δ: 6.54 (s, 2H), 5.73–5.73 (m, 1H), 5.21 (br t, 1H, J=7.3 Hz), 4.21 (s, 2H), 3.89 (3s, 9H), 3.72 (dd, 1H, J=2.6, 11.1 Hz), 3.44 (s, 3H), 3.01 (d, 1H, J=4.2 Hz), 2.58 (t, 1H, J=6.4 Hz), 2.54 (d, 1H, J=4.2 Hz), 2.43–1.83 (m, 6H), 1.75 (s, 3H) 1.67 (s, 3H) 1.23 (s, 3H) 1.15–1.04 (m, 1H).

EXAMPLE 41

Preparation of 6-O-(ethylamino)acetyl fumagillol

6-O-chloroacetyl fumagillol (130 mg), obtained from the above step 1 of the above example 1, was dissolved in dimethylformamide (1 ml), added with ethylamine (16 mg) and stirred at room temperature for 5 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 84 mg of the title compound as a colorless oil.

$^1$H-NMR (CDCl$_3$) δ: 5.72–5.70 (m, 1H), 5.21 (br t, 1H, J=7.2 Hz), 3.67 (dd, 1H, J=2.8, 11.1 Hz), 3.58–3.39 (m, 5H), 3.48 (s, 3H), 3.00 (d, 1H, J=4.3 Hz), 2.58 (t, 1H, J=6.4 Hz), 2.54 (d, 1H, J=4.3 Hz), 2.50 (q, 2H, J=11.0 Hz), 2.41–1.81 (m, 9H), 1.73 (s, 3H), 1.66 (s, 3H), 1.25 (s, 3H), 1.18–1.05 (m, 4H), 1.00 (t, 3H, J=11.0 Hz).

EXAMPLE 42

Preparation of 6-O-(isopropylamino)acetyl fumagillol

6-O-chloroacetyl fumagillol (134 mg), obtained from the above step 1 of the above example 1, was dissolved in dimethylformamide (1 ml), added with isopropylamine (22 mg) and stirred at room temperature for 5 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 93 mg of the title compound as a colorless oil.

$^1$H-NMR (CDCl$_3$) δ: 5.73–5.71 (m, 1H), 5.19 (br t, 1H, J=7.2 Hz), 3.65 (dd, 1H, J=2.8, 11.1 Hz), 3.56–3.37 (m, 5H), 3.47 (s, 3H), 3.02 (d, 1H, J=4.2 Hz), 2.59 (t, 1H, J=6.4 Hz), 2.55 (d, 1H, J=4.2 Hz), 2.50 (q, 1H, J=11.2 Hz), 2.44–1.82 (m, 9H), 1.72 (s, 3H), 1.64 (s, 3H), 1.23 (s, 3H), 1.13–1.05 (m, 7H), 1.01 (d, 1H, J=11.2 Hz).

EXAMPLE 43

Preparation of 6-O-(propylamino)acetyl fumagillol

6-O-chloroacetyl fumagillol (131 mg), obtained from the above step 1 of the above example 1, was dissolved in dimethylformamide (1 ml), added with propylamine (22 mg) and stirred at room temperature for 8 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 98 mg of the title compound as a colorless oil.

$^1$H-NMR (CDCl$_3$) δ: 5.72–5.70 (m, 1H), 5.22 (br t, 1H, J=7.2 Hz), 3.65 (dd, 1H, J=2.8, 11.1 Hz), 3.59–3.40 (m, 5H) 3.46 (s, 3H), 3.00 (d, 1H, J=4.4 Hz), 2.56 (t, 1H, J=6.4 Hz), 2.55 (d, 1H, J=4.4 Hz), 2.51 (t, 2H, J=11.0 Hz), 2.40–1.79 (m, 9H), 1.75 (s, 3H), 1.67 (s, 3H), 1.24 (s, 3H), 1.20–1.05 (m, 6H).

EXAMPLE 44

Preparation of 6-O-(1-butylamino)acetyl fumagillol

6-O-chloroacetyl fumagillol (128 mg), obtained from the above step 1 of the above example 1, was dissolved in dimethylformamide (1 ml), added with 1-butylamine (26 mg) and stirred at room temperature for 5 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 102 mg of the title compound as a colorless oil.

$^1$H-NMR (CDCl$_3$) δ: 5.73–5.71 (m, 1H), 5.21 (br t, 1H, J=7.2 Hz), 3.66 (dd, 1H, J=2.8, 11.1 Hz), 3.59–3.40 (m, 5H) 3.46 (s, 3H), 3.00 (d, 1H, J=4.3 Hz), 2.57 (t, 1H, J=6.3 Hz) 2.54 (d, 1H, J=4.3 Hz), 2.51 (t, 2H, J=11.0 Hz), 2.40–1.79 (m, 9H), 1.76 (s, 3H), 1.69 (s, 3H), 1.25 (s, 3H), 1.21–1.00 (m, 8H).

EXAMPLE 46

Preparation of 6-O-(2-methyl-butylamino)acetyl fumagillol

6-O-chloroacetyl fumagillol (130 mg), obtained from the above step 1 of the above example 1, was dissolved in dimethylformamide (1 ml), added with 2-methyl-butylamine (32 mg) and stirred at room temperature for 7 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 114 mg of the title compound as a colorless oil.

$^1$H-NMR (CDCl$_3$) δ: 5.74–5.72 (m, 1H), 5.20 (br t, 1H, J=7.1 Hz), 3.67 (dd, 1H, J=2.8, 11.1 Hz), 3.60–3.40 (m, 5H), 3.47 (s, 3H), 3.01 (d, 1H, J=4.3 Hz), 2.56 (t, 1H, J=6.3 Hz), 2.53 (d, 1H, J=4.3 Hz), 2.50 (t, 2H, J=11.2 Hz), 2.40–1.77 (m, 9H), 1.75 (s, 3H), 1.69 (s, 3H), 1.26 (s, 3H), 1.21–0.95 (m, 10H).

EXAMPLE 47

Preparation of 6-O-(2,2-dimethyl-propylamino)acetyl fumagillol

6-O-chloroacetyl fumagillol (130 mg), obtained from the above step 1 of the above example 1, was dissolved in dimethylformamide (1 ml), added with 2,2-dimethyl-propylamine (32 mg) and stirred at room temperature for 10 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 103 mg of the title compound as a colorless oil.

$^1$H-NMR (CDCl$_3$) δ: 5.73–5.70 (m, 1H)., 5.20 (br t, 1H, J=7.2 Hz), 3.67 (dd, 1H, J=2.9, 11.1 Hz), 3.57–3.36 (m, 5H), 3.46 (s, 3H), 3.00 (d, 1H, J=4.1 Hz), 2.60 (t, 1H, J=6.4 Hz), 2.55 (d, 1H, J=4.1 Hz), 2.45–1.80 (m, 10H), 1.71 (s, 3H), 1.66 (s, 3H), 1.23 (s, 3H), 1.01 (s, 9H).

EXAMPLE 50

Preparation of 6-O-(1-ethyl-propylamino)acetyl fumagillol

6-O-chloroacetyl fumagillol (130 mg), obtained from the above step 1 of the above example 1, was dissolved in dimethylformamide (1 ml), added with 1-ethyl-propylamine (32 mg) and stirred at room temperature for 6 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 99 mg of the title compound as a colorless oil.

$^1$H-NMR (CDCl$_3$) δ: 5.73–5.71 (m, 1H), 5.19 (br t, 1H, J=7.1 Hz), 3.68 (dd, 1H, J=2.7, 11.1 Hz), 3.57–3.35 (m, 5H), 3.46 (s, 3H), 3.01 (d, 1H, J=4.2 Hz), 2.58 (t, 1H, J=6.4 Hz), 2.54 (d, 1H, J=4.2 Hz), 2.52 (t, 1H, J=11.0 Hz), 2.46–1.80 (m, 9H), 1.74 (s, 3H), 1.65 (s, 3H), 1.31–1.00 (m, 14H), 1.21 (s, 3H).

EXAMPLE 54

Preparation of 6-O-(1-isopropyl-2-methylpropylamino)acetyl fumagillol

6-O-chloroacetyl fumagillol (135 mg), obtained from the above step 1 of the above example 1, was dissolved in dimethylformamide (1 ml), added with 1-isopropyl-2-methyl-propylamine (43 mg) and stirred at room temperature for 10 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 97 mg of the title compound as a colorless oil.

$^1$H-NMR (CDCl$_3$) δ: 5.73–5.70 (m, 1H), 5.19 (br t, 1H, J=7.0 Hz), 3.65 (dd, 1H, J=2.6, 11.1 Hz), 3.56–3.37 (m, 5H), 3.47 (s, 3H), 3.01 (d, 1H, J=4.3 Hz), 2.60 (t, 1H, J=6.4 Hz), 2.57 (d, 1H, J=4.3 Hz), 2.52 (d, 1H, J=11.2 Hz), 2.47–1.81 (m, 12H), 1.73 (s, 3H), 1.67 (s, 3H), 1.25 (s, 3H), 0.99 (d, 12H, J=10.8 Hz).

EXAMPLE 55

Preparation of 6-O-(3-methylbutylamino)acetyl fumagillol

6-O-chloroacetyl fumagillol (134 mg), obtained from the above step 1 of the above example 1, was dissolved in dimethylformamide (1 ml), added with 3-methylbutylamine (48 mg) and stirred at room temperature for 5 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 111 mg of the title compound as a colorless oil.

$^1$H-NMR (CDCl$_3$) δ: 5.73–5.71 (m, 1H), 5.17 (br t, 1H, J=7.0 Hz), 3.66 (dd, 1H, J=2.8, 11.1 Hz), 3.57–3.36 (m, 5H), 3.49 (s, 3H), 3.01 (d, 1H, J=4.2 Hz), 2.60 (t, 1H, J=6.4 Hz), 2.57 (d, 1H, J=4.2 Hz), 2.54–2.52 (m, 1H), 2.46–1.79 (m, 13H), 1.74 (s, 3H), 1.65 (s, 3H), 1.23 (s, 3H), 1.03–0.98 (m, 13H).

EXAMPLE 56

Preparation of 6-O-(2-methyl-allylamino)acetyl fumagillol

6-O-chloroacetyl fumagillol (129 mg), obtained from the above step 1 of the above example 1, was dissolved in dimethylformamide (1 ml), added with 2-methyl-allylamine (26 mg), and stirred at room temperature for 5 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 105 mg of the title compound as a colorless oil.

$^1$H-NMR (CDCl$_3$) δ: 5.74–5.71 (m, 1H), 5.52–5.48 (m, 2H), 5.21 (br t, 1H, J=7.2 Hz), 3.67 (dd, 1H, J=2.8, 11.1 Hz), 3.59–3.41 (m, 5H), 3.48 (s, 3H), 3.11 (br s, 2H), 3.03 (d, 1H, J=4.3 Hz), 2.57 (t, 1H, J=6.3 Hz), 2.55 (d, 1H, J=4.3 Hz), 2.40–1.77 (m, 13H), 1.79 (s, 3H), 1.74 (s, 3H), 1.65 (s, 3H), 1.22 (s, 3H).

EXAMPLE 63

Preparation of 6-O-(cyclopropylamino)acetyl fumagillol

6-O-chloroacetyl fumagillol (51.4 mg), obtained from the above step 1 of the above example 1, was dissolved in dimethylformamide (1 ml), added with cyclopropylamine (8 mg) and stirred at room temperature for 8 hours. The reaction was diluted with ethyl acetate (10 ml) and washed with saturated aqueous sodium hydrogen carbonate (3 ml) and saturated brine (3 ml). The organic layer was dried over anhydrous magnesium sulfate and filtered. The filtrate was vacuum concentrated to give the residue, which was purified by silica gel column chromatography (methanol:dichloromethane=1:10), yielding 38 mg of the title compound as a colorless oil.

$^1$H-NMR (CDCl$_3$) δ: 5.74–5.71 (m, 1H), 5.21 (br t, 1H, J=7.0 Hz), 3.64 (dd, 1H, J=2.7, 11.1 Hz), 3.57–3.39 (m, 5H), 3.48 (s, 3H), 3.00 (d, 1H, J=4.3 Hz), 2.62 (t, 1H, J=6.4 Hz) 2.56 (d, 1H, J=4.3 Hz), 2.47–1.81 (m, 7H), 1.71 (s, 3H) 1.66 (s, 3H), 1.31–1.01 (m, 5H), 1.21 (s, 3H), 0.98–0.87 (m, 1H), 0.55–0.41 (m, 2H).

EXAMPLE 64

Preparation of 6-O-(cyclobutylamino)acetyl fumagillol

6-O-chloroacetyl fumagillol (50.3 mg), obtained from the above step 1 of the above example 1, was dissolved in dimethylformamide (1 ml), added with cyclobutylamine (10 mg) and stirred at room temperature for 6 hours. The reaction was diluted with ethyl acetate (10 ml) and washed with saturated aqueous sodium hydrogen carbonate (3 ml) and saturated brine (3 ml). The organic layer was dried over anhydrous magnesium sulfate and filtered. The filtrate was vacuum concentrated to give the residue, which was purified by silica gel column chromatography (methanol:dichloromethane=1:10), yielding 40 mg of the title compound as a colorless oil.

$^1$H-NMR (CDCl$_3$) δ: 5.77–5.70 (m, 1H), 5.20 (br t, 1H, J=7.1 Hz), 3.64 (dd, 1H, J=2.8, 11.1 Hz), 3.56–3.34 (m, 6H), 3.46 (s, 3H), 3.02 (d, 1H, J=4.4 Hz), 2.61 (t, 1H, J=6.4 Hz), 2.56 (d, 1H, J=4.4 Hz), 2.48–2.37 (m, 1H), 2.21–1.60 (m, 17H), 1.74 (s, 3H), 1.64 (s, 3H), 2.22–1.01 (m, 4H), 1.19 (s, 3H).

EXAMPLE 65

Preparation of 6-O-(cyclopentylamino)acetyl fumagillol

6-O-chloroacetyl fumagillol (51.0 mg), obtained from the above step 1 of the above example 1, was dissolved in dimethylformamide (1 ml), added with cyclopentylamine (12 mg) and stirred at room temperature for 6 hours. The reaction was diluted with ethyl acetate (10 ml) and washed with saturated aqueous sodium hydrogen carbonate (3 ml) and saturated brine (3 ml). The organic layer was dried over anhydrous magnesium sulfate and filtered. The filtrate was vacuum concentrated to give the residue, which was purified by silica gel column chromatography (methanol:dichloromethane=1:10), yielding 36 mg of the title compound as a colorless oil.

$^1$H-NMR (CDCl$_3$) δ: 5.73–5.67 (m, 1H), 5.22 (br t, 1H, J=7.1 Hz), 3.62 (dd, 1H, J=2.8, 11.1 Hz), 3.57–3.36 (m, 5H), 3.44 (s, 3H), 3.21–3.10 (m, 1H), 2.99 (d, 1H, J=4.2 Hz), 2.60 (t, 1H, J=6.7 Hz), 2.55 (d, 1H, J=4.2 Hz), 2.44–2.35 (m, 1H), 2.21–1.60 (m, 15H), 1.74 (s, 3H), 1.64 (s, 3H), 1.56–1.43 (m, 2H), 1.39–1.31 (m, 2H), 1.22–1.01 (m, 4H), 1.20 (s, 3H).

EXAMPLE 66

Preparation of 6-O-(cyclohexylamino)acetyl fumagillol

6-O-chloroacetyl fumagillol (53.5 mg), obtained from the above step 1 of the above example 1, was dissolved in dimethylformamide (1 ml), added with cyclohexylamine (15 mg) and stirred at room temperature for 6 hours. The reaction was diluted with ethyl acetate (10 ml) and washed with saturated aqueous sodium hydrogen carbonate (3 ml) and saturated brine (3 ml). The organic layer was dried over anhydrous magnesium sulfate and filtered. The filtrate was vacuum concentrated to give the residue, which was purified by silica gel column chromatography (methanol:dichloromethane=1:10), yielding 42 mg of the title compound as a colorless oil.

$^1$H-NMR (CDCl$_3$) δ: 5.75–5.68 (m, 1H), 5.19 (br t, 1H, J=7.3 Hz), 3.64 (dd, 1H, J=2.8, 11.0 Hz), 3.57–3.34 (m, 6H), 3.45 (s, 3H), 3.00 (d, 1H, J=4.3 Hz), 2.61 (t, 1H, J=6.7 Hz), 2.55 (d, 1H, J=4.3 Hz), 2.46–2.33 (m, 2H), 2.23–1.57 (m, 14H), 1.76 (s, 3H), 1.63 (s, 3H), 1.36–1.02 (m, 10H), 1.20 (s, 3H).

EXAMPLE 67

Preparation of 6-O-(4-tert-butyl-cyclohexylamino)acetyl fumagillol

6-O-chloroacetyl fumagillol (128 mg), obtained from the above step 1 of the above example 1, was dissolved in dimethylformamide (1 ml), added with 4-tert-butyl-cyclohexylamine (55 mg) and stirred at room temperature for 6 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:10), yielding 104 mg of the title compound as a colorless oil.

$^1$H-NMR (CDCl$_3$) δ: 5.75–5.68 (m, 1H), 5.19 (br t, 1H, J=7.4 Hz), 3.65 (dd, 1H, J=2.7, 11.3 Hz), 3.56–3.35 (m, 6H), 3.46 (s, 3H), 3.03 (d, 1H, J=4.4 Hz), 2.61 (t, 1H, J=6.7 Hz), 2.56 (d, 1H, J=4.4 Hz), 2.46–2.33 (m, 2H), 2.23–1.72 (m, 10H), 1.78 (s, 3H), 1.65 (s, 3H), 1.36–1.19 (m, 4H), 1.21 (s, 3H), 1.16–0.94 (m, 6H), 0.82 (s, 9H).

EXAMPLE 68

Preparation of 6-O-(2-dimethylamino-1-methylethylamino)acetyl fumagillol

6-O-chloroacetyl fumagillol (132 mg), obtained from the above step 1 of the above example 1, was dissolved in dimethylformamide (1 ml), added with 2-dimethylamino-1-methylethylamine (38 mg) and stirred at room temperature for 6 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:5), yielding 104 mg of the title compound as a colorless oil.

$^1$H-NMR (CDCl$_3$) δ: 5.74–5.71 (m, 1H), 5.19 (br t, 1H, J=7.0 Hz), 3.68 (dd, 1H, J=2.7, 11.1 Hz), 3.56–3.37 (m, 5H), 3.49 (s, 3H), 3.03 (d, 1H, J=4.4 Hz), 2.91–2.88 (m, 1H), 2.65 (d, 2H, J=7.8 Hz), 2.61 (t, 1H, J=6.4 Hz), 2.56 (d, 1H, J=4.4 Hz), 2.47 (s, 6H), 2.44–1.78 (m, 10H), 1.73 (s, 3H), 1.64 (s, 3H), 1.24 (s, 3H), 1.02 (d, 3H, J=8.6 Hz).

EXAMPLES 45, 48, 49, 51–53, 57–62 AND 70–77

The fumagillol derivatives, as represented by the formula I, were prepared in the same manner as in the above example 1, except that amine compounds were changed. The results are presented in the following Table 3.

TABLE 3

| Ex. No. | Fumagillol Derivative | Amine Compound |
|---|---|---|
| 45 | 6-O-(sec-butylamino)acetyl fumagillol | sec-butylamine |
| 48 | 6-O-(pentylamino)acetyl fumagillol | Pentylamine |
| 49 | 6-O-(1-methyl-butylamino)acetyl fumagillol | 1-methyl-butylamine |
| 51 | 6-O-(1-methyl-pentylamino)acetyl fumagillol | 1-methyl-pentylamine |
| 52 | 6-O-(1,2-dimethylbutylamino)acetyl fumagillol | 1,2-dimethylbutylamine |
| 53 | 6-O-(1,2,2-trimethylpropylamino)acetyl fumagillol | 1,2,2-trimethylpropylamine |
| 57 | 6-O-(4-methyl-hepta-2,4-dienylamino)acetyl fumagillol | 4-methyl-hepta-2,4-dienylamine |
| 58 | 6-O-(1,5-dimethyl-4-hexenylamino)acetyl fumagillol | 1,5-dimethyl-4-hexenylamine |
| 59 | 6-O-(1,1-dimethyl-2-propinylamino)acetyl fumagillol | 1,1-dimethyl-2-propinylamine |
| 60 | 6-O-(prop-2-enylamino)acetyl fumagillol | prop-2-enylamine |
| 61 | 6-O-(2-bromoethylamino)acetyl fumagillol | 2-bromoethylamine |
| 62 | 6-O-(chloroethynylamino)acetyl fumagillol | chloroethynylamine |
| 70 | 6-O-(2-methoxy-2-methyl-propylamino)acetyl fumagillol | 2-methoxy-2-methyl-propylamine |
| 71 | 6-O-(2-oxo-propylamino)acetyl fumagillol | 2-oxo-propylamine |
| 72 | 6-O-(1,1-dimethyl-3-oxobutylamino)acetyl fumagillol | 1,1-dimethyl-3-oxobutylamino |
| 73 | 6-O-(ethyl-2-aminoacetate)acetyl fumagillol | ethyl-2-aminoacetate |
| 74 | 6-O-(alaninemethylesteramino)acetyl fumagillol | Alaninemethylesteramine |
| 75 | 6-O-(methyl-2-amino-3,3-dimethylbutanoate)acetyl fumagillol | methyl-2-amino-3,3-dimethylbutanoate |
| 76 | 6-O-(allylglycinemethylester)acetyl fumagillol | Allylglycinemethylester |
| 77 | 6-O-(2,2-dimethoxyethylamino)acetyl fumagillol | 2,2-dimethoxyethylamine |

Hz), 2.50 (s, 6H), 2.45–1.76 (m, 10H), 1.74 (s, 3H) 1.66 (s, 3H), 1.25 (s, 3H), 1.04 (d, 3H, J=8.1 Hz).

EXAMPLE 69

Preparation of 6-O-(2-dimethylamino-propylamino)acetyl fumagillol

6-O-chloroacetyl fumagillol (126 mg), obtained from the above step 1 of the above example 1, was dissolved in dimethylformamide (1 ml), added with 2-dimethyl-propylamine (36 mg) and stirred at room temperature for 7 hours. The reaction was diluted with ethyl acetate (20 ml) and washed with saturated aqueous sodium hydrogen carbonate (5 ml) and saturated brine (5 ml). The organic layer was dried over anhydrous magnesium sulfate and filtered. The filtrate was vacuum concentrated to give the residue, which was purified by silica gel column chromatography (methanol:dichloromethane=1:5), yielding 118 mg of the title compound as a colorless oil.

$^1$H-NMR (CDCl$_3$) δ: 5.75–5.72 (m, 1H), 5.20 (br t, 1H, J=7.0 Hz), 3.66 (dd, 1H, J=2.8, 11.1 Hz), 3.57–3.38 (m, 5H), 3.45 (s, 3H), 3.17–3.14 (m, 1H), 3.01 (d, 1H, J=4.2 Hz), 2.81 (d, 2H, J=8.4 Hz), 2.62 (t, 1H, J=6.4 Hz), 2.57 (d, 1H, J=4.2

Each of the fumagillol derivatives obtained from the above examples 63 and 64 was treated with the acid, or reacted with the salt in the presence of the acid catalyst, to perform the oxyrane ring-opening reaction.

EXAMPLE 78

Preparation of 4-((cyclopropylamino)acetyl)oxy-2-(1,2-epoxy-1,5-dimethyl-4-hexenyl)-3-methoxy-1-chloromethyl-1-cyclohexanol 6-O-(cyclopropylamino)acetyl fumagillol (100 mg), obtained from the above example 63, in tetrahydrofuran (10 ml), was added with hydrochloric acid (0.14 ml) and stirred for 32 hours. The reaction was added with water (10 ml) and ethyl acetate (100 ml). The organic layer was separated, washed with saturated brine (10 ml), dried over anhydrous magnesium sulfate and filtered. Then, the solvent was distilled off under reduced pressure to give the residue, which was purified by silica gel column chromatography (ethyl acetate:n-hexane=1:2), yielding 54 mg of the title compound as a white solid.

$^1$H-NMR (CDCl$_3$) δ: 5.77–5.70 (m, 1H), 5.20 (br t, 1H, J=7.1 Hz), 3.64 (dd, 1H, J=2.8, 11.1 Hz), 3.56–3.34 (m, 6H) 3.49 (s, 3H), 3.02 (d, 1H, J=4.4 Hz), 2.61 (t, 1H, J=6.4 Hz), 2.56 (d, 1H, J=4.4 Hz), 2.48–2.37 (m, 1H), 2.21–1.60 (m, 17H), 1.74 (s, 3H), 1.64 (s, 3H), 2.22–1.01 (m, 4H), 1.19 (s, 3H).

EXAMPLE 79

Preparation of 4-((cyclobutylamino)acetyl)oxy-2-(1, 2-epoxy-1,5-dimethyl-4-hexenyl)-3-methoxy-1-chloromethyl-1-cyclohexanol 6-O-(cyclobutylamino)acetyl fumagillol (100 mg), obtained from the above example 64, in tetrahydrofuran (10 ml) was added with chlorolithium (48 mg) and acetic acid (0.12 ml), and stirred at 30° C. for 36 hours. The reaction was added with water (10 ml) and ethyl acetate (100 ml). The organic layer was separated, washed with saturated brine (10 ml), dried over anhydrous magnesium sulfate and filtered. Then, the solvent was distilled off under reduced pressure to give the residue, which was purified by silica gel column chromatography (ethyl acetate:n-hexane=1:2), yielding 49 mg of the title compound as a white solid.

$^1$H-NMR (CDCl$_3$) δ: 5.77–5.70 (m, 1H), 5.20 (br t, 1H, J=7.1 Hz), 3.64 (dd, 1H, J=2.8, 11.1 Hz), 3.56–3.34 (m, 6H), 3.46 (s, 3H), 3.02 (d, 1H, J=4.4 Hz), 2.61 (t, 1H, J=6.4 Hz), 2.56 (d, 1H, J=4.4 Hz), 2.48–2.37 (m, 1H), 2.21–1.60 (m, 17H), 1.74 (s, 3H), 1.64 (s, 3H), 2.22–1.01 (m, 4H), 1.19 (s, 3H).

PREPARATION EXAMPLE 1

Preparation of Tablet

A tablet containing the fumagillol compound of the present invention as an effective ingredient was prepared according to the following processes.

The compound of the above example 1 was sieved, mixed with lactose, starch and pregelatinized corn starch. To the mixture, purified water was added in a suitable volume. The paste was granulated, dried, mixed with magnesium stearate, and then compressed, to obtain the tablet.

Such a tablet comprises the following components:

| | |
|---|---|
| Compound of example 1 | 5.0 mg |
| Lactose BP | 150.0 mg |
| Starch BP | 30.0 mg |
| Pregelatinized corn starch BP | 15.0 mg |
| Magnesium stearate | 1.0 mg |

PREPARATION EXAMPLE 2

Preparation of Capsule

A capsule containing the fumagillol compound of the present invention as the effective ingredient was prepared as follows.

The compound of the example 1 was mixed with a predetermined amount of a vehicle and magnesium state. Thusly obtained mixture was filled in a gelatin capsule.

Such a capsule comprises the following components :

| | |
|---|---|
| Compound of the example 1 | 5.0 mg |
| Starch 1500 | 100.0 mg |
| Magnesium sterate BP | 1.0 mg |

PREPARATION EXAMPLE 3

Preparation of Injection

An injection containing the fumagillol compound of the present invention as the effective ingredient was prepared as follows.

The compound of the example 1 was dissolved in a suitable volume of saline for injection BP. The pH of the resultant solution was controlled with dilute hydrochloric acid BP to be 3.5, and then the solution volume was controlled with saline for injection BP. The solution was filled in 5 ml type 1 ampule made of transparent glass, and the top of ampule was fused for sealing. The solution contained in the ampule was autoclaved at 120° C. for at least 15 minutes to be sterilized, giving the injection.

Such an injection comprises the following components:

| | |
|---|---|
| Compound of example 1 | 100 μg/ml |
| Dilute hydrochloric acid BP | to be pH 3.5 |
| Saline for injection BP | maximal 1 ml |

EXPERIMENTAL EXAMPLE 1

Inhibitory Effect of Fumagillol Derivative on Cell Growth

Using the HUVECs (human umbilical vein endothelial), the effect of the fumagillol derivative of the present invention on cell growth was evaluated.

The HUVECs were added to M199 medium supplemented with 20% FBS (fetal bovine serum), 100 U/ml penicillin, 100 μg/ml streptomycin, 1.5 g/L sodium bicarbonate, 0.1 mg/ml endothelial cell growth supplement (Sigma) and 0.1 mg/ml heparin (Sigma), after which the cells were incubated in an incubator at 37° C. under 5% CO$_2$. Cells were subcultured a maximum of 8 times before being discarded.

In order to evaluate inhibitory activity of the fumagillin derivative on growth of HUVECs, the inventive compound was dissolved in DMSO and its concentration was adjusted from 10 mM to 1 mM. Cells were aliquotted to 96 well plates at a density of 2×10$^3$ cells per well and incubated for about 12–24 hours to be properly attached to the plate. Thereafter, the medium was replaced with new medium. The cells were treated with the compound obtained from each of the above examples at various concentration ranges of from 10 μM to 0.001 pM, and cultured for 2–3 days, followed by removing 100 μl of the medium from each well.

Colorimetry was performed to determine the extent of cell growth. The cells on each plate was added with 20 μl of aqueous one solution and then incubated at 37° C. under 5% CO$_2$ for 2 hours. Using a 96-well plate reader, absorption was measured at 490 nm. The results are given in Table 4, below.

As such, a conventional TNP-470 having angiogenesis inhibitory effect was used as a control.

TABLE 4

| Compound | IC$_{50}$ (η g/ml) |
| --- | --- |
| TNP-470 | 29 |
| Ex. 1 | 0.0071 |
| Ex. 2 | 0.15 |
| Ex. 3 | 0.09 |
| Ex. 4 | 0.08 |
| Ex. 5 | 142 |
| Ex. 6 | 19 |
| Ex. 7 | 21 |
| Ex. 8 | 42 |
| Ex. 9 | 0.63 |
| Ex. 10 | 0.06 |
| Ex. 11 | 0.08 |
| Ex. 12 | 0.07 |
| Ex. 13 | 0.016 |
| Ex. 14 | 14 |
| Ex. 15 | 0.06 |
| Ex. 16 | 0.17 |
| Ex. 17 | 0.61 |
| Ex. 18 | 17 |
| Ex. 19 | 174 |
| Ex. 20 | 162 |
| Ex. 21 | 185 |
| Ex. 22 | 179 |
| Ex. 23 | 0.24 |
| Ex. 24 | 181 |
| Ex. 25 | 0.31 |
| Ex. 26 | 179 |
| Ex. 27 | 88 |
| Ex. 28 | 102 |
| Ex. 29 | 178 |
| Ex. 30 | 0.09 |
| Ex. 31 | 0.06 |
| Ex. 32 | 128 |
| Ex. 33 | 109 |
| Ex. 34 | 98 |
| Ex. 35 | 116 |
| Ex. 36 | 0.021 |
| Ex. 37 | 0.017 |
| Ex. 38 | 0.019 |
| Ex. 39 | 0.019 |
| Ex. 40 | 0.18 |
| Ex. 41 | 20 |
| Ex. 42 | 12 |
| Ex. 43 | 2400 |
| Ex. 44 | 3200 |
| Ex. 45 | 370 |
| Ex. 46 | 2600 |
| Ex. 47 | 16 |
| Ex. 48 | 3000 |
| Ex. 49 | 44 |
| Ex. 50 | 24 |
| Ex. 51 | 32000 |
| Ex. 52 | 290 |
| Ex. 53 | 162 |
| Ex. 54 | 11 |
| Ex. 55 | 17 |
| Ex. 56 | 28 |
| Ex. 57 | 420 |
| Ex. 58 | 415 |
| Ex. 59 | 174 |
| Ex. 60 | 185 |
| Ex. 61 | 2800 |
| Ex. 62 | 340 |
| Ex. 63 | 0.008 |
| Ex. 64 | 0.07 |
| Ex. 65 | 250 |
| Ex. 66 | 0.6 |
| Ex. 67 | 0.06 |
| Ex. 68 | 240 |
| Ex. 69 | 260 |
| Ex. 70 | 178 |
| Ex. 71 | 260 |
| Ex. 72 | 330 |
| Ex. 73 | 1200 |
| Ex. 74 | 800 |
| Ex. 75 | 2400 |
| Ex. 76 | 1490 |
| Ex. 77 | 330 |
| Ex. 78 | 0.014 |
| Ex. 79 | 0.037 |
| Intermediate | 2000 |

From the above Table 4, it can be seen that the inventive compound exhibits superior inhibitory effect on cell proliferation, compared to conventionally known fumagillin. In particular, the compound in which $R_1$ is aromatic is superior in angiogenesis inhibitory effect to the compound in which $R_1$ is aliphatic. For instance, in the case where $R_1$ is aromatic, 6-O-(4-methoxyaniline)acetyl fumagillol of the above example 1 has excellent inhibitory effect, 2000 times greater than known TNP-470. In the case where $R_1$ is aliphatic, 6-O-(cyclopropylamino)acetyl fumagillol and 6-O-(4-(cyclobutylamino)acetyl fumagillol of the above examples 63 and 64, respectively, are 100–1000 times higher in inhibitory effect on HUVEC, compared to TNP-470.

EXPERIMENTAL EXAMPLE 2

Acute Toxicity Test for Oral Administration of Fumagillol Derivative Using Rats

To investigate acute toxicity of the compound of the formula I, the following experiment was performed.

Using 6-week-old specific pathogen-free (SPF) Sprague-Dawley rats, acute toxicity was tested. Each of the compounds obtained from the above examples was suspended in 0.5% methylcelluose solution, and orally administered once to every two rats constituting each group in the dose of 1 g/kg/15 ml. After administration, mortality, clinical symptoms and body weight of the tested animals were observed. Hematological and blood-biochemical tests were carried out. The animals were dissected and abnormal conditions of pleural cavity and abdominal cavity were observed with the naked eye. As the test result, there were no specifically abnormal symptoms in any of the tested animals and no mortality. In addition, toxicity indicators were not observed in the body weight, hematological and blood-biochemical tests, or by dissection.

The present compounds did not show toxicity up to the amounts of 2 g/kg for all rats, and the minimal lethal dose (LD$_{50}$) of each compound in case of oral administration was 2 g/kg or more, thus the present compound was evaluated as a safe compound.

INDUSTRIAL APPLICABILITY

As described hereinbefore, the compound of the formula I of the present invention is advantageous in light of excellent angiogenesis inhibitory effect and low toxicity, and is usefully applicable as an angiogenesis inhibitory agent. As well, the inventive compound can inhibit cancer metastasis and treat cancer, rheumatic arthritis, psoriasis and diabetic retinopathy, which are associated with angiogenesis regarded as a pathogenic phenomenon.

The present invention has been described in an illustrative manner, and it is to be understood that the terminology used is intended to be in the nature of description rather than of limitation. Many modifications and variations of the present invention are possible in light of the above teachings.

Therefore, it is to be understood that within the scope of the appended claims, the invention may be practiced otherwise than as specifically described.

The invention claimed is:

1. A fumagillol compound represented by the following formula I, or a pharmaceutically acceptable salt thereof:

Formula I

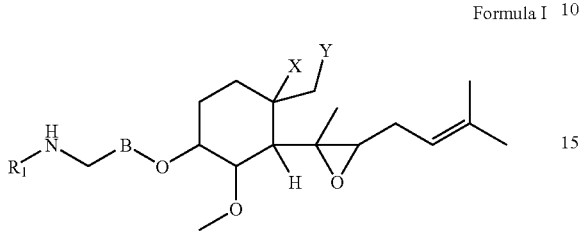

wherein,

X is —OH and Y is halogen, or X and Y are linked together to form an oxyrane ring, B represents —(C=O)— or —CH$_2$—, R$_1$ represents hydroxy; —CN; —NO$_2$; —CF$_3$; formyl; C$_1$–C$_4$ thioalkyl; acetamido; acetoxy; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_6$ alkylamino; C$_1$–C$_4$ dialkylamino; C$_1$–C$_4$ alkyloxycarboxylic acid; C$_3$–C$_6$ cycloalkyl or

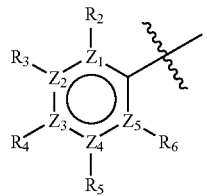

in which R$_2$, R$_3$, R$_4$, R$_5$ and R$_6$, which are the same or different, each represents hydrogen; hydroxy; —CN; —NO$_2$; —CF$_3$; formyl; C$_1$–C$_4$ thioalkyl; acetamido; acetoxy; C$_1$–C$_6$ alkyl; C$_1$–C$_4$ aminoalkyl; C$_1$–C$_4$ alkylaminoalkyl; C$_1$–C$_4$ dialkylaminoalkyl; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_6$ alkylamino; C$_1$–C$_4$ dialkylamino; C$_1$–C$_4$ hydroxyalkyl; or C$_1$–C$_4$ alkyloxycarboxylic acid; or, R$_2$ and R$_3$, R$_3$ and R$_4$, R$_4$ and R$_5$, or R$_5$ and R$_6$, are linked together to form a C$_1$–C$_3$ alkylene dioxy ring, and Z$_1$, Z$_2$, Z$_3$, Z$_4$ and Z5 each represent carbon or nitrogen.

2. The fumagillol compound as set forth in claim 1, wherein X and Y are linked together to form the oxyran ring, and B is —(C=O)—.

3. The fumagillol compound as set forth in claim 1, wherein X and Y are linked together to form the oxyran ring, B is —(C=O)—, R$_1$ is hydroxy; —CN; —NO$_2$; —CF$_3$; formyl; acetamido; acetoxy; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_6$ alkylamino; C$_1$–C$_4$ dialkylamino; C$_1$–C$_4$ alkyloxycarboxylic acid; C$_3$–C$_6$ cycloalkyl or R$_2$, R$_3$, R$_4$, R$_5$ and R$_6$, which are the same or different, each represents hydrogen; hydroxy; —CN; —NO$_2$; —CF$_3$; formyl; acetamido; acetoxy; C$_1$–C$_6$ alkyl; C$_1$–C$_4$ aminoalkyl; C$_1$–C$_4$ alkylaminoalkyl; C$_1$–C$_4$ dialkylaminoalkyl; C$_1$–C$_6$ alkoxy; C$_1$–C$_6$ aminoalkoxy; C$_1$–C$_4$ alkylaminoalkoxy; C$_1$–C$_4$ dialkylaminoalkoxy; amino; C$_1$–C$_5$ alkylamino; C$_1$–C$_4$ dialkylamino; C$_1$–C$_4$ hydroxyalkyl; or C$_1$–C$_4$ alkyloxycarboxylic acid; or R$_2$ and R$_3$, R$_3$ and R$_4$, R$_4$ and R$_5$, or R$_5$ and R$_5$ are linked together to form the C$_1$–C$_3$ alkylene dioxy ring; and Z$_1$, Z$_2$, Z$_3$, Z$_4$ and Z$_5$ each represent carbon or nitrogen.

4. The fumagillol compound as set forth in claim 1, wherein X and Y are linked together to form the oxyrane ring, B is —(C=O)—, R$_1$ is selected from the group consisting of hydroxy; chlorine; methoxy; methylpropoxy; isopropoxy; allyloxy; propyloxy; acetoxy cyano; amino; methylpropoxy; dimethylethoxy; 3,5-diisopropyl-4-methoxy; 3,5-dimethyl-4-methoxy; isopropyl-4-ethoxy; dimethylamino; ethylamino; methylenedioxy; nitro; acetoxy; trifluoromethyl; hydroxyethoxy; cyclopropyl; and cyclobutyl;

R$_2$, R$_3$, R$_4$, R$_5$ and R$_6$ is independently selected from the group consisting of hydrogen; hydroxy; methyl; chlorine; methoxy; methylpropoxy; isopropoxy; allyloxy; propyloxy; acetoxy cyano; amino; dimethylaminomethyl; methylpropoxy; dimethylethoxy; 3,5-diisopropyl-4-methoxy; 3,5-dimethyl-4-methoxy; isopropyl-4-ethoxy; dimethylamino; ethylamino; methylenedioxy; nitro; acetoxy; trifluoromethyl; and hydroxyethoxy; and Z$_1$, Z$_2$, Z$_3$ Z$_4$ and Z$_5$ each represent carbon or nitrogen.

5. The fumagillol compound as set forth in claim 1, selected from the group consisting of:

1) 6-O-(4-methoxyaniline)acetyl fumagillol;
2) 6-O-(3,4,5-trimethoxyaniline)acetyl fumagillol;
3) 6-O-(2,4-dimethoxyaniline)acetyl fumagillol;
4) 6-O-(3,4-dimethoxyaniline)acetyl fumagillol;
5) 6-O-(3,4-dimethoxy-6-nitroaniline)acetyl fumagillol;
6) 6-O-(3,4-dimethoxy-6-cyanoaniline)acetyl fumagillol;
7) 6-O-(4-allyloxyariiline)acetyl fumagillol;
8) 6-O-(4-(2-acetoxyethoxy)aniline)acetyl fumagillol;
9) 6-O-(3-cyano-4-methoxyaniline)acetyl fumagillol;
10) 6-O-(3-(dimethylaminomethyl)-4-methoxyaniline) acetyl fumagillol;
11) 6-O-(4-(2-methylpropoxyaniline)acetyl fumagillol;
12) 6-O-(3-isopropoxy-4-methoxyaniline)acetyl fumagillol;
13) 6-O-(4-(N,N-dimethylethoxy)aniline)acetyl fumagillol;
14) 6-O-(3,5-diisopropyl-4-methoxyaniline)acetyl fumagillol;
15) 6-O-(3,5-dimethyl-4-methoxyaniline)acetyl fumagillol;
16) 6-O-(3-isopropyl-4-ethoxy-6-methylaniline)acetyl fumagillol;
17) 6-O-(4-propyloxyaniline)acetyl furnagillol;
18) 6-O-(aniline)acetyl fumagillol;
19) 6-O-(4-chloroaniline)acetyl fumagillol;
20) 6-O-(4-dimethylaminoaniline)acetyl fumagillol;
21) 6-O-(4-hydroxyaniline)acetyl fumagillol;
22) 6-O-(4-aminoaniline)acetyl fumagillol;
23) 6-O-(3,4-methylenedioxyaniline)acetyl fumagillol;
24) 6-O-(4-nitroaniline)acetyl fumagillol;
25) 6-O-(2,3,4-trimethoxy-6-aminoaniline)acetyl fumagillol;

26) 6-O-(4-acetoxy-3,5-dimethoxyaniline)acetyl fumagillol;
27) 6-O-(3,4-dimethoxy-5-hydroxyaniline)acetyl fumagillol;
28) 6-O-(4-dimethylaminoethoxyaniline)acetyl fumagillol;
29) 6-O-(4-ethylaminoaniline)acetyl fumagillol;
30) 6-O-(4-ethylaminoethoxyaniline)acetyl fumagillol;
31) 6-O-(3-dimethylaminomethyl-4-methoxyaniline) acetyl fumagillol;
32) 6-O-(4-trifluoromethylaniline)acetyl fumagillol;
33) 6-O-(4-acetoxy aniline)acetyl fumagillol;
34) 6-O-(4-cyanoaniline)acetyl fumagillol;
35) 6-O-(4-hydroxyethoxyaniline)acetyl funiagillol;
36) 6-O-(5-amino-2-methoxypyridine)acetyl fumagillol;
37) 6-O-(5-methoxypyrimidine-2-amino)acetyl fumagillol;
38) 6-O-(3-methoxy-6-aminopyridazine)acetyl fumagillol;
39) 4-((4-methoxyaniline)acetyl)oxy-2-(1,2-epoxy-1,5-dimethyl-4-hexenyl)-3-methoxy-1-chloromethyl-1-cyclohexanol;
40) 4-((3,4,5-trimethoxyaniline)acetyl)oxy-2-(1,2-epoxy-1,5-dimethyl-4-hexenyl)-3-methoxy-1-chloromethyl-1-cyclohexanol;
63) 6-O-(cyclopropylamino) acetyl fumagillol;
64) 6-O-(cyclobutylamino) acetyl fumagillol;
65) 6-O-(cyclopentylamino) acetyl fumagillol;
66) 6-O-(cyclohexylamino)acetyl fumagillol;
67) 6-O-(4-tert-butylcyclohexylamino)acetyl fumagillol;
71) 6-O-(2-oxo-propylamine)acetyl fumagillol;
72) 6-O-(1,1-dimethyl-3-oxobutylamino)acetyl fumagillol;
73) 6-O-(ethyl-2-aminoacetate)acetyl fumagillol;
74) 6-O-(alanirie-methylesteramino)acetyl fumagillol;
75) 6-O-(methyl-2-amino-3,3-dimethylbutanoate)acetyl fumagillol;
76) 6-O-(allylglycine-methylester)acetyl fumagillol;
77) 6-O-(2,2-dimethoxy-ethylamino)acetyl fumagillol;
78) 4-((cyclopropylamino)acetyl)oxy-2-(1,2-epoxy-1,5-dimethyl-4-hexenyl)-3-methoxy-1-chloromethyl-1-cyclohexanol; and
79) 4-((cyclobutylamino)acetyl)oxy-2-(1,2-epoxy-1,5-dimethyl-4-hexenyl)-3-methoxy-1-chloromethyl-1-cyclohexanol.

6. A method of preparing a fumagillol compound represented by the formula 1a, comprising the following steps of:
(a) acylating a compound of the formula 2 with α-halocarboxylic acid compound in the presence of a base, to obtain a compound of the formula 3; and
(b) reacting the compound of the formula 3 with an amine compound of the formula 4, to prepare the fumagillol compound of the formula 1a via substitution:

Reaction Scheme 1

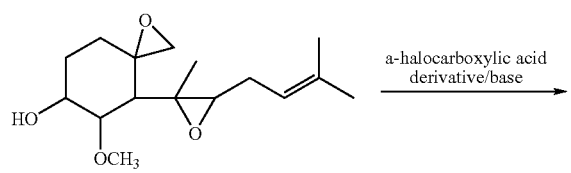

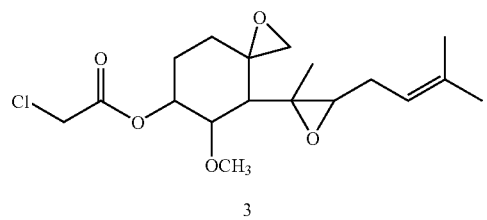

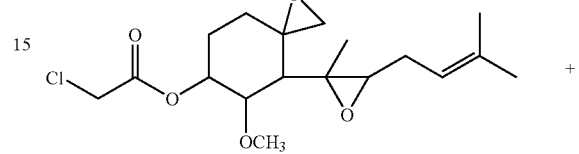

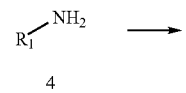

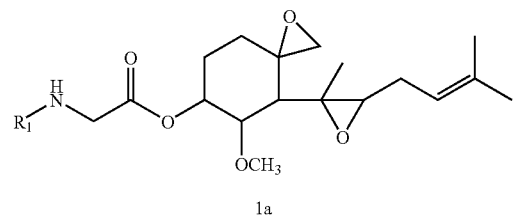

(wherein, $R_1$ is as defined in claim 1).

7. A method of preparing a fumagillol compound represented by the formula 1b, comprising the following steps of:
(a) acylating a compound of the formula 2 with α-halocarboxylic acid compound in the presence of a base, to obtain a compound of the formula 3;
(b) reacting the obtained compound of the formula 3 with an amine compound of the formula 4, to prepare the fumagillol compound of the formula 1a via substitution; and
(c) treating the fumagillol compound of the formula 1a with an acid, or reacting this compound with a salt in the presence of an acid catalyst, to perform an oxyrane ring-opening reaction, thereby preparing the fumagillol compound of the formula 1b:

Reaction Scheme 2

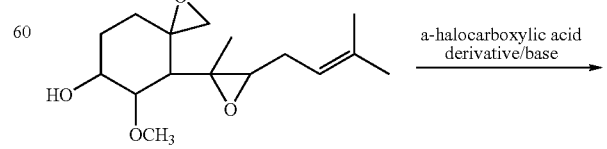

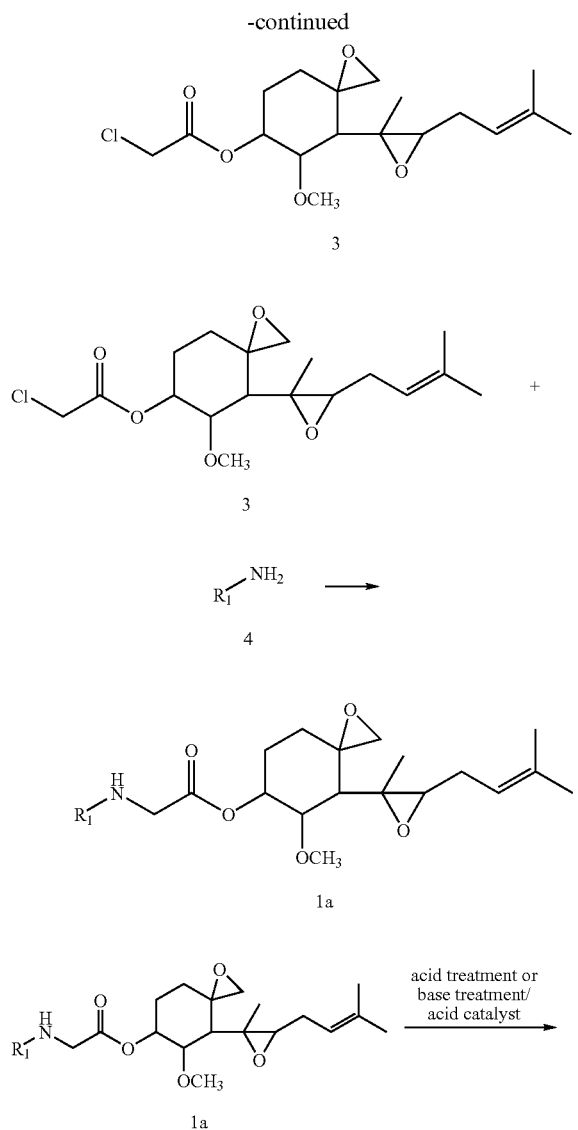

(wherein, $R_1$, X and Y are as defined in claim 1).

8. The method as set forth in claim 6 or 7, wherein α-halocarboxylic acid compound in said step (a) is selected from the group consisting of chloroacetylchloride, chloroacetylbromide, chloroacetyliodide and chloroacetylfluoride.

9. The method as set forth in claim 6 or 7, wherein the base in said step (a) is selected from the group consisting of triethylamine, diisopropyl ethylamine, pyridine and dimethylaminopyridine.

10. The method as set forth in claim 7, wherein the acid in said step (c) is selected from among hydrochloric acid, bromic acid or iodic acid, the acid catalyst is selected from the group consisting of acetic acid, sulfuric acid, paratoluene sulfonic acid, hydrochloric acid, phosphoric acid and nitric acid, and the salt is selected from the group consisting of bromolithium, chiorolithium, sodium chloride, potassium chloride, potassium bromide, sodium bromide, potassium iodide, sodium iodide and lithium iodide.

11. An intermediate for use in preparation of a compound of the formula I, as represented by the following formula II:

* * * * *